(12) United States Patent
Komorowski

(10) Patent No.: US 11,850,219 B2
(45) Date of Patent: Dec. 26, 2023

(54) INOSITOL-STABILIZED ARGININE-SILICATE FOR HAIR GROWTH AND THICKENING

(71) Applicant: NUTRITION 21, LLC, Harrison, NY (US)

(72) Inventor: James R. Komorowski, Trumbull, CT (US)

(73) Assignee: Nutrition21, LLC, Saddle Brook, NJ (US)

( * ) Notice: Subject to any disclaimer, the term of this patent is extended or adjusted under 35 U.S.C. 154(b) by 0 days.

(21) Appl. No.: 17/373,731

(22) Filed: Jul. 12, 2021

(65) Prior Publication Data

US 2021/0338606 A1 Nov. 4, 2021

Related U.S. Application Data

(63) Continuation of application No. 15/348,188, filed on Nov. 10, 2016, now abandoned.

(60) Provisional application No. 62/254,314, filed on Nov. 12, 2015.

(51) Int. Cl.
*A61K 31/155* (2006.01)
*A61K 31/7004* (2006.01)
*A61K 33/00* (2006.01)

(52) U.S. Cl.
CPC ........ *A61K 31/155* (2013.01); *A61K 31/7004* (2013.01); *A61K 33/00* (2013.01)

(58) Field of Classification Search
None
See application file for complete search history.

(56) References Cited

U.S. PATENT DOCUMENTS

| | | |
|---|---|---|
| 1,980,589 A | 11/1934 | Acree |
| 3,337,403 A | 8/1967 | Zentner |
| 4,277,488 A | 7/1981 | Mitsunaga et al. |
| 4,297,349 A | 10/1981 | Barcza |
| 4,385,052 A | 5/1983 | Zackheim et al. |
| 4,573,996 A | 3/1986 | Kwiatek et al. |
| 4,597,961 A | 7/1986 | Etscorn |
| 4,725,427 A | 2/1988 | Ashmead et al. |
| 4,839,174 A | 6/1989 | Baker et al. |
| 4,847,082 A | 7/1989 | Sabin |
| 4,908,213 A | 3/1990 | Govil et al. |
| 4,943,435 A | 7/1990 | Baker et al. |
| 5,166,168 A | 11/1992 | Stiefel |
| 5,217,997 A | 6/1993 | Levere et al. |
| 5,250,569 A | 10/1993 | Godfrey |
| 5,284,657 A | 2/1994 | Lu et al. |
| 5,288,497 A | 2/1994 | Stanley et al. |
| 5,550,249 A | 8/1996 | Della Valle et al. |
| 5,622,980 A | 4/1997 | Caldwell et al. |
| 5,626,884 A | 5/1997 | Lockett |
| 5,656,264 A | 8/1997 | Hanada et al. |
| 5,662,920 A | 9/1997 | Santus |
| 5,707,970 A | 1/1998 | McCarty et al. |
| 5,716,610 A | 2/1998 | Jack et al. |
| 5,763,392 A | 6/1998 | Hansen et al. |
| 5,763,496 A | 6/1998 | Holland |
| 5,804,203 A | 9/1998 | Hahn et al. |
| 5,840,881 A | 11/1998 | Uda et al. |
| 6,066,659 A | 5/2000 | Speck |
| 6,123,936 A | 9/2000 | Platz et al. |
| 6,132,394 A | 10/2000 | Lankinen |
| 6,156,735 A | 12/2000 | McCarty et al. |
| 6,182,655 B1 | 2/2001 | Keller et al. |
| 6,207,713 B1 * | 3/2001 | Fossel .................... A61Q 19/00 514/565 |
| 6,298,847 B1 | 10/2001 | Datta et al. |
| 6,344,444 B1 | 2/2002 | McCarty et al. |
| 6,387,394 B1 | 5/2002 | Baichwal et al. |
| 6,418,926 B1 | 7/2002 | Chawla |
| 6,462,051 B1 | 10/2002 | Nozawa et al. |
| 6,660,251 B1 | 12/2003 | Bunger et al. |
| 6,709,868 B2 | 3/2004 | Law et al. |
| 6,803,456 B1 | 10/2004 | Kuhlmann |
| 7,238,373 B2 | 7/2007 | Meyrowitz |
| 7,576,132 B2 | 8/2009 | Juturu et al. |
| 8,524,279 B2 | 9/2013 | Snyder et al. |
| 8,779,007 B2 | 7/2014 | Kropke et al. |
| 8,835,487 B2 | 9/2014 | Sedel |
| 9,339,467 B2 | 5/2016 | Beyerinck et al. |
| 9,351,961 B2 | 5/2016 | Sedel |
| 10,959,971 B2 | 3/2021 | Komorowski |

(Continued)

FOREIGN PATENT DOCUMENTS

CN 1842318 A 10/2006
EP 056902 A2 8/1982

(Continued)

OTHER PUBLICATIONS

Machine translation of EP1040815 (A1), published Oct. 4, 2000. (Year: 2000).*
Machine translation of DE20315174(U1), published Nov. 12, 2003. (Year: 2003).*
Otani, JP 2004099599 A, Apr. 2, 2004, machine translation. (Year: 2004).*
Seymour, American Journal of Physiology-Legacy Content 78.2 (1926): 281-286. (Year: 1926).*
Ansel's Pharmaceutical Dosage Forms and Drug Delivery Systems, 8th Edition, Allen et al. eds., Lippincott Williams & Wilkins, Philadelphia, PA, 2005.

(Continued)

*Primary Examiner* — Layla D Berry
(74) *Attorney, Agent, or Firm* — Foley Hoag LLP; Lucas P. Watkins; Benjamin A. Vaughan

(57) ABSTRACT

The present invention generally relates to compositions and methods for topical or transdermal delivery, for promoting wound healing, reducing scarring, and/or promoting hair growth. Specifically, the present disclosure is directed to a topical arginine silicate formulation that demonstrates surprising improvements in promoting hair growth.

20 Claims, 10 Drawing Sheets

(56) References Cited

U.S. PATENT DOCUMENTS

| | | | |
|---|---|---|---|
| 11,103,000 | B2 | 8/2021 | Komorowski |
| 11,246,886 | B2 | 2/2022 | Komorowski |
| 2002/0068365 | A1 | 6/2002 | Kuhrts |
| 2002/0123504 | A1 | 9/2002 | Redmon et al. |
| 2002/0132800 | A1 | 9/2002 | Popp et al. |
| 2003/0028169 | A1 | 2/2003 | Fossel |
| 2004/0009746 | A1 | 1/2004 | Korman |
| 2004/0097467 | A1 | 5/2004 | Juturu et al. |
| 2004/0204387 | A1 | 10/2004 | McLaurin |
| 2005/0048012 | A1 | 3/2005 | Jermann et al. |
| 2006/0020007 | A1 | 1/2006 | Berlin |
| 2006/0115555 | A1 | 6/2006 | Foulger et al. |
| 2006/0204455 | A1 | 9/2006 | Giniger |
| 2007/0020206 | A1 | 1/2007 | Jermann et al. |
| 2007/0116831 | A1 | 5/2007 | Prakash et al. |
| 2007/0149442 | A1 | 6/2007 | Rubin |
| 2007/0292493 | A1 | 12/2007 | Brierre |
| 2009/0104171 | A1 | 4/2009 | Pardee et al. |
| 2010/0291195 | A1* | 11/2010 | Fossel .................. A61Q 7/00 424/450 |
| 2011/0123553 | A1 | 5/2011 | Mi et al. |
| 2012/0064126 | A1 | 3/2012 | Sung et al. |
| 2012/0141588 | A1 | 6/2012 | Chopra et al. |
| 2012/0238498 | A1 | 9/2012 | Endo |
| 2013/0101569 | A1 | 4/2013 | Weston |
| 2013/0296390 | A1 | 11/2013 | Nelson |
| 2014/0011255 | A1 | 1/2014 | Ying et al. |
| 2014/0030331 | A1 | 1/2014 | Sedel |
| 2014/0364461 | A1 | 12/2014 | Karnik |
| 2016/0081959 | A1 | 3/2016 | Bartos et al. |
| 2016/0263135 | A1 | 9/2016 | Komorowski et al. |
| 2017/0000809 | A1 | 1/2017 | Komorowski |
| 2017/0135969 | A1 | 5/2017 | Komorowski |
| 2017/0348235 | A1 | 12/2017 | White |
| 2018/0071264 | A1 | 3/2018 | Nelson et al. |
| 2020/0078394 | A1 | 3/2020 | Komorowski |
| 2020/0155510 | A1 | 5/2020 | Komorowski |
| 2021/0100776 | A1 | 4/2021 | Nelson et al. |
| 2022/0265704 | A1 | 8/2022 | Komorowski |

FOREIGN PATENT DOCUMENTS

| | | |
|---|---|---|
| EP | 1911357 A1 | 4/2008 |
| EP | 2805730 | 11/2014 |
| FR | 2610522 | 8/1989 |
| FR | 2745498 | 9/1997 |
| JP | S60 094949 A | 5/1985 |
| JP | S6125688 B2 | 6/1986 |
| JP | H04 169528 A | 6/1992 |
| JP | 2001/181211 A | 7/2001 |
| JP | 2007/503407 A | 2/2007 |
| JP | 2013/529623 A | 7/2013 |
| JP | 2015/522630 A | 8/2015 |
| MX | MX-2019/011848 A | 3/2021 |
| WO | WO-98/34647 | 8/1998 |
| WO | WO-00/45651 | 8/2000 |
| WO | WO-02/28379 | 4/2002 |
| WO | WO-2004/017913 | 3/2004 |
| WO | WO-2007/13655 A1 | 2/2007 |
| WO | WO-2011/161421 A1 | 12/2011 |
| WO | WO-2012/173808 | 12/2012 |
| WO | WO-2014/016003 A1 | 1/2014 |
| WO | WO-2017/004226 | 1/2017 |
| WO | WO-2018/045244 A1 | 3/2018 |
| WO | WO-2018/076108 A1 | 5/2018 |
| WO | WO-2020/051428 A1 | 3/2020 |
| WO | WO-2020/102203 A1 | 5/2020 |

OTHER PUBLICATIONS

Asai et al., "Topical application of ex vivo expanded endothelial progenitor cells promotes vascularization and wound healing in diabetic mice," International Wound Journal, 2012: pp. 527-533.

Ask the dentist, how often should I go to the dentist for a teeth cleaning? [online], [retrieved Jul. 21, 2018]. Retrieved from the Internet: <URL: https://askthedentist.com/how-often-should-i-go-to-the-dentist-for-a-teeth-cleaning/>.

Bassler, "Hard water, food fibre, and silicon," British Medical Journal, 1978; 1: p. 919.

Bonnefont-Rousselot, "Glucose and reactive oxygen species," Curr. Opin. Clin. Nutr. Metab. Care, 2002; 5: pp. 561-568.

Calles-Escandon et al., "Diabetes and endothelial dysfunction: A clinical perspective." Endocrine Reviews, 2001; 22(1): pp. 36-52.

Calver et al., "Effect of local intra-arterial NG -monomethyl-L-arginine in patients with hypertension: the nitric oxide dilator mechanism appears abnormal," J. of Hypertension, 1992; 10: pp. 1025-1031.

Carlisle et al., "A silicon requirement for normal growth of cartilage in culture," Fed. Proc., 1980; 39: p. 787.

Carlisle, "Biochemical and morphological change associated with long bone abnormalities in silicon deficiency," J. Nutr., 1980; 110: pp. 1046-1055.

Carlisle, "In vivo Requirement for Silicon in Articular Cartilage and Connective Tissue Formation in the Chick," J. Nutr., 1976; 106: pp. 478-484.

Carlisle, "Silicon: An Essential Element for the Chick," Science, 1972; 178: pp. 619-621.

Chen et al., "L-Arginine Abrogates Salt-sensitive Hypertension in Dah/Rapp Rats," J. Clin. Invest., 1991; 88: pp. 1559-1567.

Cherian et al., "L-arginine and Free Radical Scavengers Increase Cerebral Blood Flow and Brain Tissue Nitric Oxide Concentrations after Controlled Cortical Impact Injury in Rats," J. of Neurotrauma, 2003; 20(1): pp. 77-85.

Clarkson et al., "Oral L-Arginine Improves Endothelium-dependent Dilation in Hypercholesterolemic Young Adults," J. Clin. Invest., 1996; 97(8): pp. 1989-1994.

Clowes et al., "Suppression by heparin of smooth muscle cell proliferation in injured arteries," Nature, 1977; 265: pp. 625-626.

Cooke et al., "Is NO an Endogenous Antiatherogenic Molecule," Arteriosclerosis and Thrombosis, 1994; 14(5): pp. 653-655.

Cosgrove, "Nitric Oxide Ingredients for Sports," Nutritional Outlook, [online], Nov. 8, 2013. Retrieved from the Internet: <URL: http://www.nutritionaloutlook.com/heart-health/nitric- oxide-ingredients-sports>.

Creager et al., "L-Arginine Improves Endothelium-dependent Vasodilation in Hypercholesterolemic Humans," J. Clin. Invest., 1992; 90: pp. 1248-1253.

Curtis et al., "Nitric oxide supplementation or synthesis block-which is the better approach to treatment of heart disease?," Trends in Pharmacological Sciences, 1997; 18(7): pp. 239-244.

Drexler et al., "Correction of endothelial dysfunction in coronary microcirculation of hypercholesterolaemic patients by L-arginine," Lancet, 1991; 338: pp. 1546-1550.

Edelman et al., "Effect of controlled adventitial heparin delivery on smooth muscle cell proliferation following endothelial injury," Proc. Natl. Acad. Sci. USA, 1990; 87: pp. 3773-3777.

Eisinger et al., "Effects of silicon, fluoride, etidronate and magnesium on bone mineral density: a retrospective study," Magnisium Research, 1993; 6(3): pp. 247-249.

Garson et al., "Organosilicon Entities as Prophylactic and Therapeutic Agents," J. of Pharmaceutical Sciences, 1971; 60(8): pp. 1113-1127.

Geoffrey Stark, DDS, How much toothpaste per brushing is recommended? [online], [retrieved Jul. 23, 2018]. Retrieved from the Internet: <URL: https://secure.advantagedental.com/images/files/faq_toothpaste.htm>.

Goodman and Gilman's: The Pharmacological Basis of Therapeutics, 8th Ed., Gilman et al., eds., Pergamon Press, Elmsford, NY, 1990.

Greenhalgh et al., "PDGF and FGF stimulate wound healing in the genetically diabetic mouse," American Journal of Pathology, 1990; 136(6):1235-1246.

Guyton et al., "Inhibition of rat arterial smooth muscle cell proliferation by heparin," Circ. Res., 1980; 46: pp. 625-634.

(56) References Cited

OTHER PUBLICATIONS

Harrison's Principles of Internal Medicine, 13th edition, vol. 2, Isselbacher et al. (eds.), published 1994 by McGraw-Hill in 1994, p. 1321.
Hott et al., "Short-term effects of organic silicon on trabecular bone in mature ovariectomized rats," Calcif. Tissue Int., 1993; 53: pp. 174-179.
International Search Report and Written Opinion dated Aug. 26, 2016 in PCT/US16/040128.
International Search Report and Written Opinion dated Jan. 27, 2020 in PCT/US19/58653.
International Search Report and Written Opinion dated Mar. 8, 2021 in PCT/US20/65418.
Kelly et al., "Insulin resistance: lifestyle and nutritional interventions," Alternative Medicine Review, 2000; 5(2): pp. 109-132.
Kelly et al., "L-Theanine and Caffeine in Combination Affect Human Cognition as Evidenced by Oscillatory alpha-Band Activity and Attention Task Performance," J. Nutr., 2008; 138(8): pp. 1572S-1577S.
Kottke et al., Chapter 10: Tablet Dosage Forms, in Modern Pharmaceutics, 4th Edition, Banker et al., eds., Marcel Dekker, Inc., New York NY, 2002: pp. 287-333.
Laurant et al., "Dietary L-Arginine Attenuates Blood Pressure in Mineralocorticoid-Salt Hypertensive Rats," Clin. and Exper. Hypertension, 1995; 17(7): pp. 1009-1024.
Im-Emsap et al., Chapter 9: Disperse Systems, in Modern Pharmaceutics, 4th Edition, Banker et al., eds., Marcel Dekker, Inc., New York NY, 2002: pp. 237-285.
Loeper et al., "The Antiatheromatous Action of Silicon," Atherosclerosis, 1979; 33: pp. 397-408.
Loeper et al., "The Physiological Role of the Silicon and its Antiatheromatous Action, in Biochemistry of Silicon and Related Problems," Bendz G. et al. Eds..Plenum Press, NY, 1978; pp. 281-296.
Luscher, "Endothelium-derived nitric oxide: The endogenous nitrovasodilator in the human cardiovascular system," Eur. Heart J., 1991; 12(Suppl. E): pp. 2-11.
Marsh et al., "Relationships Among Balance, Visual Search, and Lacrosse-Shot Accuracy," J Strength Cond Res, 2010; 24(6): pp. 1507-1514.
Maulik et al., "Nitric Oxide signaling in ischemic heart," Cardiovasc. Res., 1995; 30(4): pp. 593-601.
McPherson et al., "Superoxide activates constitutive nitric oxide synthase in a brain particulate fraction," Biochemical and Biophysical Research Communications, 2002; 296: pp. 413-418.
Miller et al., "Practical Clinical Application of Biochemical Markers of Bone Turnover," Journal of Clinical Densitometry, 1999; 2(3): pp. 323-342.
Mind Lab Pro®, "Nootropics for Ganiers—Level Up Your Ganiing \Nith Cognitive Enhancers," Nootropics for Gamers—Level Up Your Gaming with Cognitive Enhancers, 2018, [online], [retrieved on Dec. 18, 2019]. Retrieved from the Internet: <URL: https://www.mindlabpro.com/blogs/nootropics/nootropics-gamers-gaming>.
Moncada et al., "The L-Arginine-Nitric Oxxide Pathway," The New. Engl. J. of Med., 1993; 329(27): pp. 2002-2012.
Nitric Oxide Benefits, Supplements, Sources, and Side Effects, [online], [dated May 24, 2015]. Retrieved from the Internet: <URL: https://web.archive.org/web/20150524100645/http://www.nitricoxide.org: 80/>.
Nitrosigine Launch, [online], [dated May 16, 2013]. Retrieved from the Internet: <URL: https://nutrition21.com/nutrition-21-launches-nitrosigine-a-novel-patented-source-of-inositol- stabilized-arginine-silicate-accepted-by-the-fda-as-a-new-dietary-ingredient/>.
Nutrition 21, Inc., EurekAlert!, [online], public release Dec. 13, 2007. Retrieved from the Internet: <URL: https://www.eurekalert.org/pub_releases/2007-12/n2-ncd121207.php>.
Parr, "Silicon, Wine, and the Heart," Lancet, 1980; p. 1087.
Partial European Search Report for European Application No. 03793307.4, dated Aug. 2, 2007.
Pharmaceutical Dosage Forms: Tablets, Lieberman et al., eds., Marcel Dekker, Inc., New York, NY, 1989.
Proctor et al., "Metabolic effects of a novel silicate inositol complex of the nitric oxide precursor arginine in the obese insulin-resistant JCR:LA-cp rat," Metabolism Clinical and Experimental, 2007; 56: pp. 1318-1325.
Proctor et al., "A novel complex of arginine-silicate improved micro and macrovascular function and inhibits glomerular sclerosis in insulin-resistant JCR:LA-cp rats," Diabetologia, 2005; 48(9): pp. 1925-1932.
Rood-Ojalvo et al., "The benefits of inositol-stabilized arginine silicate as a workout Ingredient," Journal of the International Society of Sports Nutrition, 2015; 12(suppl. 1): p. 14.
Rubanyi, "Endothelium-Derived Vasoactive Factors in Health and Disease, in Cardiovascular Significance of Endothelium-Derived Vasoactive Factors," Rubanyi, G.M., ed., Futura Publishing Company, Inc., NY xi-xix, 1991.
Salt metathesis reaction, Wikipedia [online], [retrieved 2018]. Retrieved from the Internet: <URL: https://en.wikipedia.org/wiki/Salt_metathesis_reaction>.
Saul, [online], [retrieved on Nov. 27, 2017]. Retrieved from the Internet: <URL: <http://www.doctoryourself.com/fatigue.html>, 2005.
Schiffman et al., "Taste of nutrients: amino acids, vitamins and fatty acids," Perception & Physcophisics, 1975; 17(2): pp. 140-146.
Schwarz et al., "Growth-promoting Effects of Silicon in Rats," Nature, 1972; 239: pp. 333-334.
Schwarz et al., "Inverse Relation of Silicon in Drinking Water and Atherosclerosis in Finland," Lancet, 1977; pp. 538-539.
Schwarz, "Significance and Functions of Silicon in Warm-Blooded Animals, in Biochemistry of Silicon and Related Problems," Bendz, G. et al., Eds., Plenum Press, NY 207-230 (1978).
Schwarz, "Silicon, Fibre, and Atherosclerosis," Lancet, 1977; pp. 454-457.
Supplementary European Search Report for European Application No. EP 03793307.4 dated Dec. 4, 2008.
Svehla, "Reaction of Silicates," Vogels Textbook of Macro and Semimicro Qualitative Inorganic Analysis 5th Edition, Longman, London, 1979; pp. 350-353.
Toker et al., "The effects of hydrogen sulphide on alveolar bone loss in periodontitis," Minerva Stomatol, 2014; 63(4): pp. 103-110.
Tsao et al., "Enhanced endothelial adhesiveness in hypercholesterolemia is attenuated by L- arginine," Circulation, 1994; 89(5): pp. 2176-2182.
Van Lente, "Markers of inflammation as predictors in cardiovascular disease," Clinica Chimica Acta., 2000; 293: pp. 31-52.
Wang et al. "Effects of nitric oxide synthase inhibitors on systemic hypotension, cytokines and inducible nitric oxide synthase expression and lung injury following indotoxin administration in rats," J. Biomed. Sci., 1999; 6: pp. 28-35.
Wilson et al., "Impaired cognitive function and mental performance in mild dehydration," European Journal of Clinical Nutrition, 2003; 57(2): pp. S24-S29.
Al-Qazzaz et al.; "Cognitive impairment and memory dysfunction after a stroke diagnosis: a post-stroke memory assessment," Neuropsychiatric Disease and Treatment, 2014; 10: 1677- 1691.
Carlson et al.; "Predictors of neurocognitive outcomes on antiretroviral therapy after cryptococcal meningitis: a prospective cohort study," Metabolic brain disease, 2014; 29(2): pp. 269-279.
Edmonds et al.; "Water consumption, not expectancies about water consumption, affects cognitive performance in adults," ELSEVIER, Appetite, 2013; 60: pp. 148-153.
Hoogman et al.; "Cognitive outcome in adults after bacterial meningitis," Journal of Neurology, Neurosurgery & Psychiatry, 2007; 78(10): pp. 1092-1096.
Hung et al.; "Cognitive Decline among Patients with Chronic Obstructive Pulmonary Disease," American Journal of Respiratory and Critical Care Medicine, 2009; 180(2): pp. 134-137.
Kirkorian et al.; "Improved cognitive-cerebral function in older adults with chromium supplementation," Nutritional Neuroscience, 2010; 13(3): pp. 116-122.
Kumar et al.; "Promising Therapeutics with Natural Bioactive Compounds for Improved Learning and Memory—A Review of Randomized Trials," Molecules, 2012; 17: pp. 10503-10539.

(56) References Cited

OTHER PUBLICATIONS

Kurmann et al.; "Progressive multifocal leukoencephalopathy in common variable immunodeficiency: mitigated course under mirtazapine and mefloquine," Journal of neurovirology, 2015; 21(6): pp. 694-701.
Lockhart et al.; "Cognition enhancing or neuroprotective compounds for the treatment of cognitive disorders: why? when? which?" ELSEVIER; Experimental Gerontology, 2003; 38: pp. 1119-1128.
Adams et al., "Effect of a vitamin/mineral supplement on children and adults with autism," BMC Pediatrics, Dec. 2011; 11 (111), [retrieved on Oct. 8, 2019]. Retrieved from the Internet: <URL: https://bmcpediatr.biomedcentral.com/track/pdf/10.1186/1471-2431-11-111>.
Adams et al., "Nutritional and metabolic status of children with autism vs. neurotypical children, and the association with autism severity," Nutrition & Metabolism, 2011; 8(34): pp. 1-32.
Berge et al. "Pharmaceutical Salts" Journal of Pharmaceutical Sciences, 1977, vol. 66, No. 1, pp. 1-18.
Biotin sodium salt: retrieved from: <https://pubchem.ncbi.nlm.nih.gov/compound/Biotin-sodium-salt> Create Date Sep. 10, 2008 (Retrieved on Aug. 19, 2020).
Biotinate: retrieved from: <https://pubchem.ncbi.nlm.nih.gov/compound/Biotinate> Create Date May 23, 2006 (Retrieved on Aug. 19, 2020).
Blum et al., "Toxicologic evaluation of a novel, highly soluble biotin salt, magnesium biotinate" Food and Chemical Toxicology, vol. 153: p. 112267 (2021).
Blum et al.: Toxicologic evaluation of a novel, highly soluble biotin salt, magnesium biotinate, Food and Chemical Toxicology, 153, 2021, 112267 (Year: 2021).
Carboy et al. "Disease-modifying therapies for multiple sclerosis" Current Treatment Options in Neurology, 2003, vol. 5, pp. 35-54.
Cicek et al., "The Protective Effects of a Combination of an Arginine Silicate Complex and Magnesium Biotinate Against UV-Induced Skin Damage in Rats" Frontiers in Pharmacology, vol. 12, Article 657207 (2021).
Deans, "Targeted Diet Interventions in Autistic Spectrum Disorders," [online], 2014, pp. 1-2, [retrieved on Feb. 16, 2021 ]. Retrieved from the Internet: <URL: https://www.psychologytoday.com/sg/blog/evolutionary-psychiatry/201402/targeted-diet-interventions-in-autistic-spectrum-disorders-0>.
Demir et al., "Effects of a Combination of Arginine Silicate Inositol Complex and a Novel Form of Biotin on Hair and Nail Growth in a Rodent Model" Biological Trace Element Research, 201:751-765 (2023).
Durmas et al., "Arginine Silicate Inositol Complex Accelerates Cutaneous Wound Healing" Biological Trace Element Research, 177: 122-131 (2017).
International Search Report and Written Opinion for PCT/US2017/049757, dated Nov. 7, 2017.
International Search Report and Written Opinion issued in connection with PCT/US2019/049915, dated Nov. 12, 2019.
International Search Report and Written Opinion issued in PCT/US2019/060932, dated Jan. 29, 2020.
Kalman et al., "A Randomized Double-Blind Evaluation of a Novel Biotin and Silicon Ingredient Complex on the Hair and Skin of Healthy Women" Journal of Clinical & Experimental Dermatology Research, vol. 12, issue 1, No. 551 (2021).
Khaibullin et al., "Elevated Levels of Proinflammatory Cytokines in Cerebrospinal Fluid of Multiple Sclerosis Patients," May 18, 2017 (May 18, 2017), Front. Immunol., 2017; 8(531): pp. 1-10.
Modern Biotechnology: vol. 2, Editors-in-Chief CHU Ju and LI Yourong.—Shanghai: East China University of Science and Technology Press, Mar. 2008: pp. 293-294.
Ojalvo et al., "Pharmacokinetics of a Novel Form of Biotin, Magnesium Biotinate, in Healthy Subjects (P06-027-19)", Current Developments in Nutrition, 2019; vol. 3(1): p. 537.
Ojalvo et al., "The Safety and Absorption of Magnesium Biotinate in Rats (P06-029-19)", Current Developments in Nutrition, 2019; 3(1): p. 539.
Pharmaceutics, Editors-in-Chief: CHEN Weiwei, et al. - Xi'an Jiaotong University Press. Dec. 2013: pp. 6-8.
Pourabdolhossein et al., "Nogo Receptor Inhibition Enhances Functional Recovery following Lysolecithin-Induced Demyelination in Mouse Optic Chiasm," Plos One, 2014; 9(9): pp. 1-13.
Quick Reference Guide for Drugs Used for Skin Diseases, Editor-in-Chief, MAO Wei'an.—Beijing: Jindun Publishing House, Apr. 2014; p. 316.
Sahin et al., "Effects of magnesium biotinate supplementation on serum insulin, glucose and lipid parameters along with liver protein levels of lipid metabolism in rats" Magnesium Research, 23(1): 9-19 (2021).
Simons et al., "Can psychiatric childhood disorders be due to inborn errors of metabolism?" Eur Child Adolesc Psychiatry, 2017; 26: pp. 143-154.
Spilioti et al., "Evidence for treatable inborn errors of metabolism in a cohort of 187 Greek patients with autism spectrum disorder (ASD)," Frontiers in Human Neuroscience, 2013; 7(858): pp. 1-7.
Su et al., "Experimental Measurement and Modeling of the Solubility of Biotin in Six Pure Solvents at Temperatures from 298.15 K to 333.85 K," J. Chem. Eng. Data, 2014; 59: pp. 3894-3899.
Supplementary European Search Report issued in EP 17847596 dated Mar. 17, 2020.
Sylla et al., "An Open-label Experience Trial to Evaluate the Effects of a Novel Supplement and Hair Serum Combination on Hair Skin and Nails in Healthy Women" Current Developments in Nutrition, vol. 5, Issue Supplement 2, p. 374 (2021).
Tourbah et al., "MD1003 (high-dose biotin) for the treatment of progressive multiple sclerosis: A randomised, double-blind, placebo-controlled study," Multiple Sclerosis Journal, 2016; 22(13): pp. 1719-1731.
U.S. Department of Health and Human Services, FDA, "Guidance for Industry: Q3C Impurities: Residual Solvents," Dec. 1997.
University of California—Davis Health System. "Children with autism have mitochondrial dysfunction, study finds." ScienceDaily, Nov. 30, 2010 [retrieved on Oct. 18, 2019]. Retrieved from the Interne<https://www.sciencedaily.com/releases/2010/11/101130161521.htm>.
Wang et al., "Spatial Memory Impairment Is Associated with Hippocampal Insulin Signals in Ovariectomized Rats," PLOS One, 2014; 9(8): pp. 1-7.
Wikipedia, "Clinically isolated syndrome," Jul. 17, 2018, [online]. Retrieved on Jan. 8, 2020 from <https://en.wikipedia.org/wiki/Clinically_isolated_syndrome>.
Wikipedia, "Multiple sclerosis", Jul. 26, 2018, [online]. Retrieved on Jan. 8, 2020 from <https://en.wikipedia.org/wiki/Multiple_sclerosis>.
Wu Mao-ying et al., "New Technology for Synthesis of Magnesium Stearate," Science & Technology in Chemical Industry, 2000; 8(6): pp. 43-45. (English translation provided.).
Zaffanello et al., "A Case of Partial Biotinidase Deficiency Associated With Autism," Child Neuropsychology, 9(3):184-188 (2010).
Zempleni et al., "Biotin biochemistry and human requirements," The Journal of Nutritional Biochemistry, 1999; 10: p. 128-138.
Ahmad et al., "Treatment of Pyruvate Carboxylase Deficiency With High Doses of Citrate and Aspartate" American Journal of Medical Genetics, vol. 87, pp. 331-338 (1999).
Al-Owain et al., "Autism Spectrum Disorder in a Child with Propionic Acidemia" JIMD Reports, vol. 7, pp. 63-66 (2012).
International Search Report and Written Opinion for International Application No. PCT/US2023/014077 dated May 23, 2023.
Komorowsky et al., "The effect of combination of an Arginine Silicate Complex and Magnesium Biotinate on hair and nail growth in rats (P06-026-19)", Curr Dev Nutr 3.Suppl 1 (2019).
Mirmiran et al., "Dietary L-arginine intakes and the risk of metabolic syndrome: a 6-year follow-up in tehran lipid and glucose study", *Preventive Nutrition and Food Science* 22(4): 263 (2017).
Prescha et al., "Dietary silicon and its impact on plasma silicon levels in the Polish population", *Nutrients* 11(5): 980 (2019).

(56) References Cited

OTHER PUBLICATIONS

Roth et al., "Prenatal Administration of Biotin in Biotin Responsive Multiple Carboxylase Deficiency" Pediatric Research, vol. 16, pp. 126-129 (1982).
Serajuddin, "Salt formation to improve drug solubility", Advanced drug delivery reviews 59.7 (2007): 603-616.

* cited by examiner

INOSITOL-STABILIZED ARGININE-SILICATE FOR HAIR GROWTH AND THICKENING

CROSS-REFERENCE TO RELATED APPLICATIONS

This application is a continuation of U.S. application Ser. No. 15/348,188 filed on Nov. 10, 2016, which claims priority to of U.S. Provisional Application No. 62/254,314 filed on Nov. 12, 2015, the contents of each of which is incorporated by reference herein in their entirety.

BACKGROUND

Field

The present invention generally relates to compositions and methods for topical or transdermal delivery, for promoting wound healing, reducing scarring, and/or promoting hair growth.

Description of the Related Art

When barriers are broken, infections occur. Surgery, trauma (for example, scrapes, lacerations, punctures, abrasions, and burns), medical instrumentation (for example, catheterization, ventilation), chronic wounds (for example, diabetic foot ulcers) and a variety of diseases disrupt our natural barriers of defense. Wounds may become contaminated with microbes and may provide an excellent environment for microbial growth. Bleeding and leakage may provide fluids and nutrients that ultimately support microbial growth. Bacterial or fungal colonization, and/or overt infection may occur. Various surgical, trauma and medical settings all involve disruption of our natural barriers of defense and deserve special attention because the outcomes can range from rapid cure, to cure with heavy scarring, to lethal sepsis.

Antimicrobial treatment of early infections may alter the course of the infection, resulting in more resistant and more dangerous infections. Common antimicrobial strategies focus on the use of selective antibiotics (for example, penicillin for gram-positive organisms) in order to avoid the development of bacteria that are resistant to broad-spectrum antibiotics. Inadvertently, this important strategy can have negative outcomes on an individual patient, where targeted antibiotics result in the emergence of an aggressive, different microorganism (for example, *Pseudomonas*). In this way, treated wounds can become the site for a "parade of pathogens", where an early, dominant microbial species (for example, *Staph aureus*) is replaced by a second (for example, MRSA, methicillin-resistant *Staph aureus*) and, perhaps, even a third and fourth microbial species (for example, a multi-drug resistant gram negative species).

Ultimately, the original natural barrier is the ideal defense against such infections. Current methods of wound closure, such as suturing and grafting have limited success; both methods leave the subject vulnerable to infection, and the subject will likely have significant scarring resulting from these procedures. Accordingly, improved methods for promoting wound healing are needed.

Arginine silicate can be produced by combining arginine, a silicate salt and inositol. Although the products described herein may contain other agents in addition to arginine and silicate, they are referred to throughout the specification as "arginine silicate." Arginine silicate can be synthesized, for example, by reacting arginine (free base), potassium silicate and (optionally) inositol. Thus, the compositions described herein may contain arginine, silicate, and inositol—which may be referred to throughout the specification as "inositol-stabilized arginine silicate," "arginine silicate," "arginine silicate inositol," "ASI," "arginine-silicate-inositol complex," or "complex."

SUMMARY

The present disclosure is directed to a topical arginine silicate formulation that demonstrates surprising improvement in wound healing time leading to more advantageous recovery and reducing hospital costs. Such formulations may also lessen scarring. The formulations may, for example, be applied to skin or to mucous membranes to facilitate wound healing.

Embodiments disclosed herein relate to the use of compositions comprising, consisting essentially of, or consisting of arginine, a silicate salt and inositol, arginine-silicate-inositol complexes, or combinations thereof, including pharmaceutically acceptable salts, hydrates, solvates, or mixtures thereof for topical application and for use in, for example, wound healing treatments, treatments to reduce wound scarring, or treatments to reduce inflammation. Embodiments disclosed herein also relate to the use of compositions comprising, consisting essentially of, or consisting of arginine, a silicate salt and inositol, arginine-silicate-inositol complexes, or combinations thereof, including pharmaceutically acceptable salts, hydrates, solvates, or mixtures thereof for topical application and for use in, for example, simulating and/or promoting hair growth.

In some embodiments, the formulation is a gel. In some embodiments, the formulation is a cream. In some embodiments, the formulation is a lotion. In some embodiments, the formulation is an ointment. In some embodiments, the formulation is a salve. In some embodiments, the formulation is a balm. In some embodiments, the formulation is a suspension. In some embodiments, the formulation is an emulsion. In some embodiments, the formulation is a foam. In some embodiments, the formulation is a solution. In some embodiments, the formulation is embedded, dispersed, coated, or deposited onto or in an adhesive patch. In some embodiments, the formulation is embedded, dispersed, coated, or deposited onto or in a solid "stick," (that can be rubbed or sprayed onto the skin).

In some embodiments, the formulation is a hair care product. In some embodiments, the formulation is a shampoo. In some embodiments, the formulation is a conditioner. In some embodiments, the formulation is a leave-in conditioner. In some embodiments, the formulation is a mousse. In some embodiments, the formulation is a pomade. In some embodiments, the formulation is a hair spray.

In some embodiments, the formulation contains from about 2% to about 8% arginine silicate (w/w), from about 2% to about 7% arginine silicate (w/w), from about 2% to about 6% arginine silicate (w/w), from about 2% to about 5% arginine silicate (w/w), from about 2% to about 4% arginine silicate (w/w), from about 3% to about 4% arginine silicate (w/w), or about 4% arginine silicate (w/w).

In some embodiments, the formulation contains about 2.1% arginine silicate (w/w). In some embodiments, the formulation contains about 2.2% arginine silicate (w/w). In some embodiments, the formulation contains about 2.3% arginine silicate (w/w). In some embodiments, the formulation contains about 2.4% arginine silicate (w/w). In some embodiments, the formulation contains about 2.5% arginine silicate (w/w). In some embodiments, the formulation contains about 2.6% arginine silicate (w/w). In some embodiments, the formulation contains about 2.7% arginine silicate (w/w). In some embodiments, the formulation contains about 2.8% arginine silicate (w/w). In some embodiments, the formulation contains about 2.9% arginine silicate (w/w). In some embodiments, the formulation contains about 3.0% arginine silicate (w/w). In some embodiments, the formulation contains about 3.1% arginine silicate (w/w). In some embodiments, the formulation contains about 3.2% arginine silicate (w/w). In some embodiments, the formulation contains about 3.3% arginine silicate (w/w). In some embodiments, the formulation contains about 3.4% arginine silicate (w/w). In some embodiments, the formulation contains about 3.5% arginine silicate (w/w). In some embodiments, the formulation contains about 3.6% arginine silicate (w/w). In some embodiments, the formulation contains about 3.7% arginine silicate (w/w). In some embodiments, the formulation contains about 3.8% arginine silicate (w/w). In some embodiments, the formulation contains about 3.9% arginine silicate (w/w). In some embodiments, the formulation contains about 4.0% arginine silicate (w/w). In some embodiments, the formulation contains about 4.1% arginine silicate (w/w). In some embodiments, the formulation contains about 4.2% arginine silicate (w/w). In some embodiments, the formulation contains about 4.3% arginine silicate (w/w). In some embodiments, the formulation contains about 4.4% arginine silicate (w/w). In some embodiments, the formulation contains about 4.5% arginine silicate (w/w). In some embodiments, the formulation contains about 4.6% arginine silicate (w/w). In some embodiments, the formulation contains about 4.7% arginine silicate (w/w). In some embodiments, the formulation contains about 4.8% arginine silicate (w/w). In some embodiments, the formulation contains about 4.9% arginine silicate (w/w). In some embodiments, the formulation contains about 5.0% arginine silicate (w/w). In some embodiments, the formulation contains about 5.1% arginine silicate (w/w). In some embodiments, the formulation contains about 5.2% arginine silicate (w/w). In some embodiments, the formulation contains about 5.3% arginine silicate (w/w). In some embodiments, the formulation contains about 5.4% arginine silicate (w/w). In some embodiments, the formulation contains about 5.5% arginine silicate (w/w). In some embodiments, the formulation contains about 5.6% arginine silicate (w/w). In some embodiments, the formulation contains about 5.7% arginine silicate (w/w). In some embodiments, the formulation contains about 5.8% arginine silicate (w/w). In some embodiments, the formulation contains about 5.9% arginine silicate (w/w). In some embodiments, the formulation contains about 6.0% arginine silicate (w/w). In some embodiments, the formulation contains about 6.1% arginine silicate (w/w). In some embodiments, the formulation contains about 6.2% arginine silicate (w/w). In some embodiments, the formulation contains about 6.3% arginine silicate (w/w). In some embodiments, the formulation contains about 6.4% arginine silicate (w/w). In some embodiments, the formulation contains about 6.5% arginine silicate (w/w). In some embodiments, the formulation contains about 6.6% arginine silicate (w/w). In some embodiments, the formulation contains about 6.7% arginine silicate (w/w). In some embodiments, the formulation contains about 6.8% arginine silicate (w/w). In some embodiments, the formulation contains about 6.9% arginine silicate (w/w). In some embodiments, the formulation contains about 7.0% arginine silicate (w/w). In some embodiments, the formulation contains about 7.1% arginine silicate (w/w). In some embodiments, the formulation contains about 7.2% arginine silicate (w/w). In some embodiments, the formulation contains about 7.3% arginine silicate (w/w). In some embodiments, the formulation contains about 7.4% arginine silicate (w/w). In some embodiments, the formulation contains about 7.5% arginine silicate (w/w). In some embodiments, the formulation contains about 7.6% arginine silicate (w/w). In some embodiments, the formulation contains about 7.7% arginine silicate (w/w). In some embodiments, the formulation contains about 7.8% arginine silicate (w/w). In some embodiments, the formulation contains about 7.9% arginine silicate (w/w). In some embodiments, the formulation contains about 8.0% arginine silicate (w/w). Ranges of concentrations are also contemplated, and may include ranges from or between any two of the foregoing values.

In some embodiments the arginine silicate is complexed. In some embodiments the arginine silicate is complexed with inositol. In some embodiments, the arginine silicate is not complexed.

In some embodiments the molar ratio of arginine to silicate is between about 1:4 and 4:1. In some embodiments the molar ratio of arginine to silicate is between about 1:3 and 3:1. In some embodiments the molar ratio of arginine to silicate is between about 1:2 and 2:1. In some embodiments the molar ratio of arginine to silicate is about 1:1.

In some embodiments the molar ratio of arginine to silicate to inositol is between about 1:1:1 and 3:3:2. In some embodiments the molar ratio of arginine to silicate to inositol is between about 1:1:1 and 2:2:3. In some embodiments the molar ratio of arginine to silicate to inositol is between about 1:1:1 and 2:2:1. In some embodiments the molar ratio of arginine to silicate to inositol is between about 1:1:1 and 2:2:1.5. In some embodiments the molar ratio of arginine to silicate to inositol is about 1:1:1.

The actual dose of arginine silicate described herein depends on the specific compound, and on the specific composition and method of delivery. In some embodiments, a daily dose may be from about 1.0 mg/kg to about 2,500 mg/kg or more of body weight, from about 2.0 mg/kg or less to about 2,000 mg/kg, from about 3.0 mg/kg to about 1,500 mg/kg of body weight, from about 4.0 mg/kg to about 1,000 mg/kg of body weight, from about 5.0 mg/kg to about 500 mg/kg of body weight, from about 6.0 mg/kg to about 200 mg/kg of body weight, from about 7.0 mg/kg to about 100 mg/kg of body weight, from about 8.0 mg/kg to about 50 mg/kg of body weight, from about 9.0 mg/kg to about 20 mg/kg of body weight, or from about 10 mg/kg to about 15 mg/kg of body weight.

In some embodiments the composition is applied once per day. In some embodiments the composition is applied at least twice per day. In some embodiments the composition is applied at least three times per day. In some embodiments the composition is applied at least four times per day.

In some embodiments, the composition is applied directly to the wound. That is to say, in some aspects, the ASI containing composition is placed into direct contact with the wound area with no intervening materials or compositions in between the composition and the wound. In some embodiments, the composition is applied indirectly to the wound, e.g. on a bandage or patch. Thus, in some aspects, a patch or patch may include ASI as an active ingredient. In some embodiments, the composition is applied in the area surrounding the wound. In some embodiments, the composition is applied directly to the wound and to the areas surrounding the wound. In some embodiments, the wound is in skin. In other embodiments, the wound is in a mucous membrane.

In some embodiments, wound healing time is decreased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, or by about 99%.

In some embodiments, scarring is decreased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, or by about 99%.

In some embodiments, the composition is applied to non-wounded tissue. In some embodiments, the composition is applied to the scalp. In some embodiments, the composition promotes hair growth. In some embodiments, hair growth is promoted at a shaved area. In some embodiments, hair growth is promoted after treatment with chemotherapy. In some embodiments, hair growth in promoted in balding areas. In some embodiments, the composition increases the rate of hair growth. In some embodiments, the composition increases hair thickness. Use for facilitating or promoting hair growth may be done in conjunction with wound healing or independent of wound healing, and may be applied to broken or unbroken skin to facilitate hair growth.

The compositions disclosed herein may be used for decreasing wound healing time, decreasing wound scarring, promoting hair growth, and/or reducing inflammation. In some aspects, a method for decreasing wound healing time includes applying a topical composition comprising an effective amount of ASI to a wound, wherein the amount decreases wound healing time in comparison to not applying the composition. In some aspects, a method for decreasing wound scarring includes applying a topical composition comprising an effective amount of ASI to a wound, wherein the amount decreases scarring from the wound in comparison to not applying the composition. In some aspects, a method for promoting hair growth includes applying a topical composition comprising an effective amount of ASI to a treatment area on a mammalian subject, wherein the amount promotes hair growth in the treatment area in comparison to non-treatment areas. In some aspects, a method for reducing inflammation includes applying a topical composition comprising an effective amount of ASI to a treatment area on a mammalian subject, wherein amount reduces inflammation in the treatment area in comparison to non-treatment areas.

BRIEF DESCRIPTION OF THE DRAWINGS

FIG. 4: Is a bar graph showing the effect of topical application of different doses of ASI on inducible nitric oxide synthase (iNOS) levels at 5th, 10th and 15th days after wound formation.

FIG. 5: Is a bar graph showing the effect of topical application of different doses of ASI on endothelial nitric oxide synthase (eNOS) at 5th, 10th and 15th days after wound formation.

FIG. 6: Is a bar graph showing the effect of topical application of different doses of ASI on collagen levels at 5th, 10th and 15th days after wound formation.

FIG. 7: Is a bar graph showing the effect of topical application of different doses of ASI on matrix metalloproteinase-2 (MMP-2) levels at 5th, 10th and 15th days after wound formation.

FIG. 8: Is a bar graph showing the effect of topical application of different doses of ASI on matrix metalloproteinase-9 (MMP-9) levels at 5th, 10th and 15th days after wound formation.

FIG. 9: Is a bar graph showing the effect of topical application of different doses of ASI on vascular endothelial growth factor (VEGF) levels at 5th, 10th and 15th days after wound formation.

FIG. 10: Is a bar graph showing the effect of topical application of different doses of ASI on endothelial growth factor (EGF) levels at 5th, 10th and 15th days after wound formation.

FIG. 11: Is a bar graph showing the effect of topical application of different doses of ASI on fibroblast growth factor (FGF) levels at 5th, 10th and 15th days after wound formation.

FIG. 13: Is a bar graph showing the effect of topical application of different doses of ASI on NFκB levels at 5th, 10th and 15th days after wound formation.

FIG. 14: Is a bar graph showing the effect of topical application of different doses of ASI on TGF-β levels at 5th, 10th and 15th days after wound formation.

FIG. 15: Is a bar graph showing the effect of topical application of different doses of ASI on TNF-α levels at 5th, 10th and 15th days after wound formation.

FIG. 16: Is a bar graph showing the effect of topical application of different doses of ASI on and IL-10 levels at 5th, 10th and 15th days after wound formation.

DESCRIPTION

Figure 1:
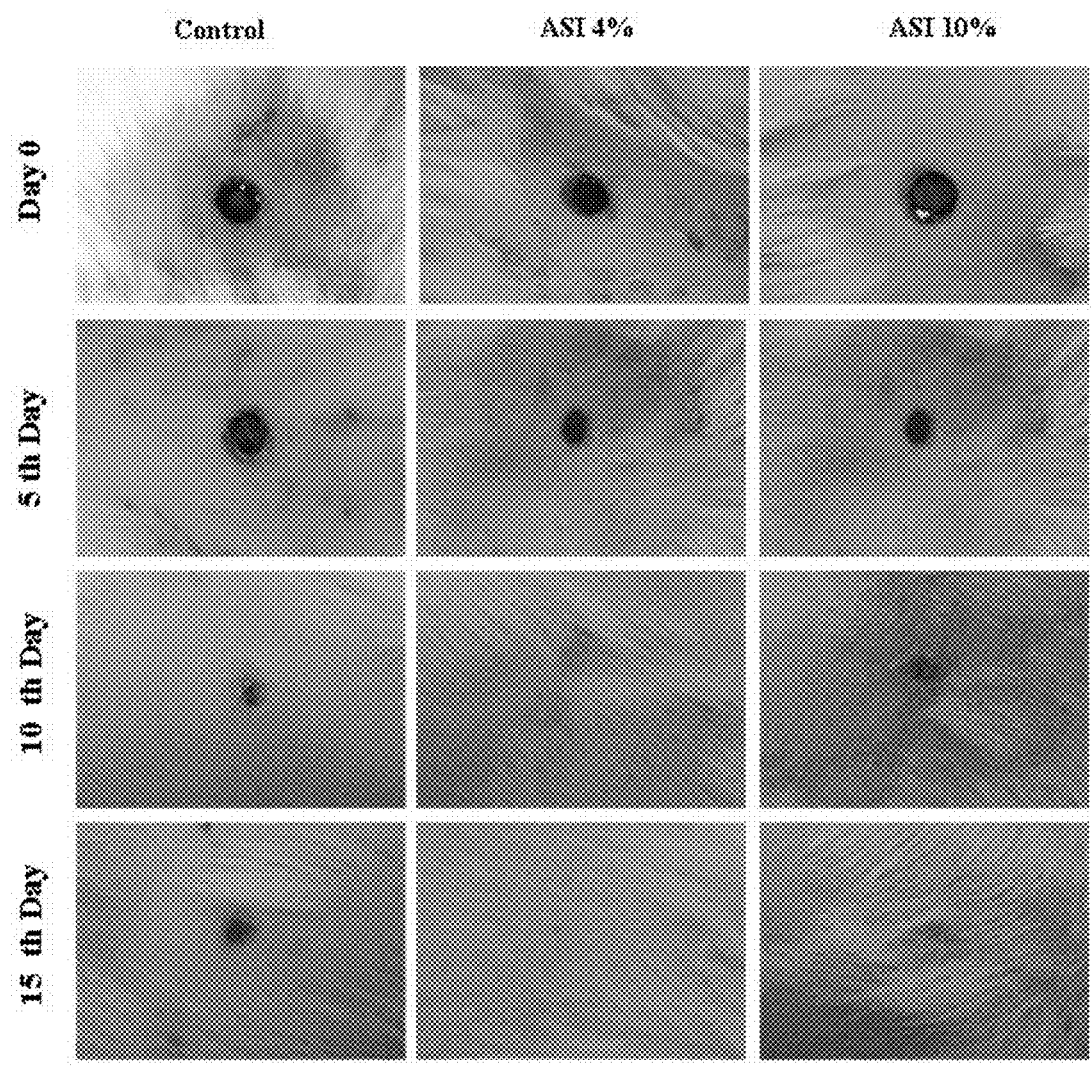
FIG. 1: Is a set of photographs of the dorsal surface of test rats demonstrating decreased time to wound healing from a laceration upon treatment with a topical arginine-silicate-inositol composition (ASI). Representative rats from the control group (no treatment), ASI 4% group (topical application of 4.4% ASI (w/w)), and ASI %10 group (topical application of 10% ASI (w/w)) one day 0, 5, 10, and 15 are shown.

This disclosure provides compositions and methods of promoting wound healing, including topical and transdermal delivery of arginine silicate. The composition can take the form of a gel, a cream, a lotion, an ointment, a solution, a suspension, a mousse, an emulsion, a solid "stick," etc., that can be rubbed or sprayed onto the skin, for example, wounded skin. Other aspects of the present invention are generally directed to methods of making or using such compositions, methods of promoting such compositions, and kits including such compositions.

Arginine silicate inositol complex ("ASI") is a composition of arginine, silicon and inositol that has been reported for its beneficial effects on vascular health. This disclosure reports the beneficial effect of the composition on wound healing in rats.

For example, in rats with excision wounds, the granulation tissue was found to form significantly slower in the control group than in the ASI treated rats (4% or 10% ASI ointment (w/w), twice per day). The mean unhealed wound area was significantly smaller and the mean percentage of total wound healing was significantly higher in ASI-treated wounds than in the control wound. Hydroxyproline, collagen and matrix metalloproteinases were measured in the granulated tissue and found to be affected. Inducible nitric oxide synthase (iNOS), endothelial nitric oxide synthase (eNOS), collagen, matrix metalloproteinase 2 (MMP-2), MMP-9, vascular endothelial growth factor (VEGF), fibroblast growth factor (FGF), epidermal growth factor (EGF), nuclear factor kappa-light-chain-enhancer of activated B cells (NF-κB), and various cytokines (TNF-α and IL-1β) measured in this study showed a significant fall in expression level in ASI-treated wounds. The results indicate that a topical application of ASI has beneficial effects on the healing response of wounds.

The healing of wounds involves a cascade of events characterized by the restructuring of the damaged tissue in an attempt to restore as normal a condition as possible. The process involves considerable complex factors involving the synthesis of the matrix components and cross talks/interactions between several factors such as the cytokines and growth factors. In this study, we studied a number of macroscopic, microscopic changes and the changes at the molecular level in excision wound treated with ASI at two different dose levels in a rather simple and reproducible animal model.

Synthesis of hydroxyproline and the deposition of collagen observed in the proliferative stage of the healing process is a hallmark of wound healing. The hydroxyproline content, as well as the collagen determined at the site of wound, increased progressively in ASI treated animals on day 5, 10 and 15 after the injury when compared with control group. The results corroborated with the histology of the skin tissue from the treated rats.

Tissue remodeling is regulated by proteinases and their inhibitors at the levels of expression, deposition, inhibition and activation. In particular, matrix metalloproteinase-9 (MMP-9) is believed to function in the remodeling of the basement membrane zone, because several extracellular matrix proteins in the basement membrane zone, such as type IV collagen, have been identified as substrates of this proteinase.

MMPs are well known to increase during acute wound healing and it has been shown that a prolonged and excessive production of MMPs (MMP-9 in particular) leads to disordered wound healing.

In this study, it was observed that MMP-2 and MMP-9 expression in wound sites decreased in ASI treated groups. MMP-2 and MMP-9 expression of ASI treated groups significantly decreased in 5, 10 and 15 days after injury compared with control group. MMP-9 synthesis and secretion are strictly controlled, and can be induced by a variety of physiological stimuli, including cytokines, chemokines and growth factors. Moreover, stress-related chemical and physical factors, such as X-ray radiation, UV light, pH change, and reactive oxygen species, are also known to modulate MMP-9 production in cells.

Angiogenesis plays a major role in tissue repair and remodeling. Angiogenic factors, such as vascular endothelial cell growth factor (VEGF) or basic fibroblast growth factor (bFGF), enhance the proliferation and/or migration of endothelial cells (ECs) both in vitro and in vivo. These actions of ECs are associated with proteolytic degradation of the extracellular matrix (ECM), which enables ECs to migrate or invade the interstitial space. Plasminogen activators (PAs) convert inactive zymogen plasminogen to the active protease plasmin, which not only degrades fibrin and several ECM proteins, but also activates pro-collagenase to collagenase, a matrix metalloproteinase (MMP). Similarly, the growth factors such as PDGF, TGBβ, and bFGF are pivotal in normal wound repair, driving cell migration, protein synthesis, proliferation, matrix formation, and generally controlling the repair process. The biological activity of many of these growth factors is enhanced by the presence of specific matrix proteins.

Increased vascular permeability has since been shown to occur during the early phases of wound repair, theoretically allowing deposition of the fibrin-rich matrix necessary for cellular migration. The identification of increased vascular permeability concomitant with increased VEGF production in skin wounds provided evidence for a role for VEGF in wound repair. VEGF production and VEGF-mediated angiogenic activity would rise in the early hypoxic wound and then fall when neovascularization is complete and wound perfusion is restored.

Previous studies have attempted to correlate the levels of growth factors to the stage of wound healing. The observed levels of individual factors do appear to correspond to the stage of wound healing. It has been reported that the primary sources of surgical wound VEGF are the fibroblast and the macrophage. VEGF has been associated with angiogenesis in numerous pathological situations, including rheumatoid arthritis, tumor growth and, proliferative retinopathy, the angiogenic process being initiated by bFGF and maintained by VEGF.

The pro-inflammatory cytokines IL-6, TNF-α, and IL-1β all showed high levels on day 1 corresponding to the initial inflammatory response. IL-6 levels then decreased down to day 8, TNF-α levels remained static, and IL-1β levels showed a second peak on postoperative day 6, which may correspond to its other functions in wound healing, for example, matrix synthesis and collagen production. In this study, postoperatively at the 5th, 10th and 15th days, VEGF, EGF and FGF levels were increased in ASI treated groups. These results indicate the role of VEGF in the wound healing.

Inflammation results in a continuous generation of reactive species, such as the non-radical hydrogen peroxide or the superoxide radical. Nuclear Factor-κB (NF-κB) was determined to play an essential role in inflammation. NF-κB is activated by numerous different stimuli, including protein kinase C activators, cytokines, oxidants, and viruses. Excessive NF-κB activation has been implicated in many disease states associated with chronic inflammation, such as asthma, ulcerative colitis, and joint inflammation. It has been reported that inhibition of NF-κB may reduce inflammation by reducing the local NOx concentrations, and they showed that chronic administration of a recombinant adenovirus expressing an NF-κB super repressor significantly increases the amount of collagen accumulation in subcutaneously implanted polyvinyl alcohol sponges.

In the current report, levels of NF-κB were significantly decreased and collagen deposition levels were significantly increased in ASI treated groups. The mechanism of this phenomenon may be from decreasing inflammation through the inhibition of NF-κB. NF-κB inhibition effect of ASI may have helped to enhance wound healing.

In conclusion, the results of the present disclosure suggest that the effects of ASI on wound healing depended on the dose. Beneficial effects were evident after treatment with 4% ASI (w/w), but were lost after 10% ASI (w/w). The results suggest that topical application of 4% ASI (w/w) have beneficial effects on wound healing.

Administration and Compositions

Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound. The amount of carrier employed in conjunction with the compound is sufficient to provide a practical quantity of material for administration per unit dose of the compound. One having ordinary skill in the art would understand additional techniques and compositions for making dosage forms useful in the methods described herein.

The composition for topical and transdermal delivery can take the form of a gel, a cream, a lotion, an ointment, a solution, a suspension, an emulsion, or embedded, dispersed, coated, or deposited onto an adhesive patch or a solid "stick," (that can be rubbed or sprayed onto the skin). Topical formulations may generally be comprised of a pharmaceutical carrier, co-solvent, emulsifier, penetration enhancer, preservative system, and emollient. Where the formulation is to be applied to mucous membrane, the formulation may advantageously include a thickener or mucoadhesive.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. One having ordinary skill in the art would understand additional considerations for inclusion of various components in pharmaceutical compositions.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of the obroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

Compositions described herein may optionally include other active ingredients.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

Methods of Promoting Wound Healing and/or Reducing Scarring

Some embodiments of the present invention include methods of promoting wound healing with the compositions comprising compounds described herein. Some embodiments of the present invention include methods of reducing scarring with the compounds and compositions comprising compounds described herein. Some methods include administering a compound, composition, pharmaceutical composition described herein to a subject in need thereof. In some embodiments, a subject can be an animal, for example, a mammal, a human.

"Subject" as used herein, means a human or a non-human mammal, for example, a dog, a cat, a mouse, a rat, a cow, a sheep, a pig, a goat, a non-human primate or a bird, for example, a chicken, as well as any other vertebrate or invertebrate. In some embodiments, the subject is a human.

In some embodiments a subject in need of the present invention is a subject with an injury or wound to a tissue. Such tissues include, but are not limited to, epithelial tissue, epidermis, dermis, hypodermis, and subcutaneous connective tissue. The types of wounds include, but are not limited to, lesions, burns, lacerations, abrasions, surgical wounds, and punctures.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In some embodiments, administration in combination is accomplished by combining the agents in a single dosage form. In some embodiments, the agents are administered sequentially. In some embodiments, the agents are administered through the same route, such as topically. In some embodiments, the agents are administered through different routes, such as one being administered topically and another being administered orally.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1

Animals:

In this study, 42 male, 4 months old, Wistar albino rats weighing between 250 and 300 g were used. Animals were housed at 21° C. with a day/night cycle of 12 h. During the study these animals were fed ad libitum standard rodent feed. Guidelines for the care and use of animals approved by the relevant institution were followed and the local ethics committee approved this study.

Anesthesia:

The rats were anaesthetized with single intramuscular injection of 6 mg/kg xylazine hydrochloride (Rompun, Bayer, 23.32 mg/ml) and 85 mg/kg ketamine hydrochlorure (Ketalar, Parke-Davis, 50 mg/ml).

Test Drugs:

4% and 10% arginine-silicate inositol (ASI)(w/w) ointment, and cold cream (Botafarma, 12.5% spermaceti+12% white wax+56% liquid paraffin+0.5% borate of soda+19% distilled water) were used in this study.

Wound Model:

The dorsal surfaces of the rats were shaved and prepared with 10% antiseptic povidone-iodine solution (Kim-Pa, Pov-iiodeks, % 10 povidone-iodine). Then a disposable 1 cm diameter skin punch biopsy tool (Acuderm Inc., Fort Lauderdale, FL) was used to create a full-thickness excisional wound.

The rats were divided into 2 main groups such that each group had 21 randomly selected rats. Each main group was divided within themselves into 3 subgroups of 7 rats each to perform postoperative 5, 10 and 14 days of examination. Immediately after the wounds were made, the wounded areas in the first (n=21) and second (n=21) was covered with cold cream (Botafarma, 12.5% spermaceti+12% white wax+ 56% liquid paraffin+0.5% borate of soda+19% distilled water) (Control) and 4% or 10% ASI ointment twice a day, respectively. These applications were repeated every day. The wounds were clinically observed in all groups every day. The rats that completed postoperative follow-up periods of 5 (7 rats from each group), 10 (7 rats from each group) and 14 days (7 rats from each group) will be sacrificed.

Measurements:

On every bandage change, the wound boundaries were traced on a transparent sheet with a fine-tipped permanent marker. These transparent sheets were scanned and the areas of wound sites and epithelization fronts were measured with the help of the paint-brush (PB) computer program. The data obtained was calculated with the following formula: Area $(cm^2)=P/K \cdot M$, where P is the value of a particular wound site obtained on the PB, K is a rate constant for expressing the values of the PB as $cm^2$, and M is the magnitude of tracings after scanning.

During the qualitative examination, the expansion rate, the day wound contraction started, the fraction of the wound healed with contraction, the rate of wound contraction, the day epithelization was first noticed, the fraction of wound healed with epithelization (final wound size) and the number of days in which wound healing was fully completed was evaluated. The statistical comparison was made with ANOVA. The results were considered significant at $P<0.05$ and a 95% confidence interval (Kiliç et al., 2002). These data are shown in Tables 1-5 and FIGS. 1-16.

Histopathological Examination:

Burned skin tissue samples were collected after sacrificing the rats for histopathological examination purposes. These tissue samples were fixed in 10% neutral buffered formalin solution, embedded in paraffin wax, cut into 5

μm-thick sections and stained with haematoxyline-eosin and Masson's trichrome stain for examination by light microscopy.

Histological scoring was assigned in a blinded manner as described previously (Greenhalgh et al., 1990; Asai et al., 2013). Briefly, each specimen was given a score of 1-12: 1-3, none to minimal cell accumulation and granulation tissue or epithelial migration; 4 to 6, thin, immature granulation dominated by inflammatory cells, but with few fibroblasts, capillaries or collagen deposition and minimal epithelial migration; 7-9, moderately thick granulation tissue, ranging from domination by inflammatory cells to more fibroblasts and collagen deposition; and 10-12, thick vascular granulation tissue dominated by fibroblasts and extensive collagen deposition.

Statistical Analyses:

The thickness of granulation tissue was examined and recorded at the center of each wound. Statistically, all data are expressed in millimeters as mean±standard error. The differences between days 5, 10 and 14 was compared using the Mann Whitney U test. The differences between groups was compared using the Kruskal-Wallis test. Statements of statistical significance are based on $P<0.05$. These analyses were carried out using SPSS statistical analysis system (Release 10.0, SPSS. Inc.).

TABLE 1

Changes in wound sizes ($mm^2$) during the healing periods

| Groups | 0 (n = 21) | 5 (n = 21) | 10 (n = 14) | 15 (n = 7) |
|---|---|---|---|---|
| Control | 19,625 | 15.33 | 3.21 | 1.86 |
| ASI—I 4% | 19,625 | 8.90 | 0.31 | 0.17 |
| ASI—II 10% | 19,625 | 9.52 | 0.50 | 0.29 |

Control: Control group no treatment.
ASI 4%: Topical application of 4.4% ASI (w/w)
ASI % 10: Topical application of 10% ASI (w/w)

TABLE 2

Effect of topical application of ASI on wound area (%)

| Groups | 5 (n = 21) | 10 (n = 14) | 15 (n = 7) |
|---|---|---|---|
| Control | 78.13 | 16.38 | 9.46 |
| ASI—I 4% | 45.37 | 1.57 | 0.85 |
| ASI—II 10% | 48.53 | 2.55 | 1.46 |

Wound area (%) = (Wound area at day X/Wound area at day 0) × 100.
Control: Control group no treatment.
ASI 4%: Topical application of 4.4% ASI (w/w)
ASI % 10: Topical application of 10% ASI (w/w)

TABLE 3

Effect of topical application of ASI on percent of wound contraction

| Groups | 5 (n = 21) | 10 (n = 14) | 15 (n = 7) |
|---|---|---|---|
| Control | 21.87 | 83.62 | 90.54 |
| ASI—I 4% | 54.63 | 98.43 | 99.15 |
| ASI—II 10% | 51.47 | 97.45 | 98.54 |

Percent of wound contraction on day X = 100—percentage of wound area on day X
Control: Control group no treatment.
ASI 4%: Topical application of 4.4% ASI (w/w)
ASI % 10: Topical application of 10% ASI. = (w/w)

TABLE 4

Changes in wound sizes of three groups during the healing periods ($mm^2$).

| Groups | Rats | 0 | 5 | 10 | 15 |
|---|---|---|---|---|---|
| Control | 1-A | 19,625 | 15 | — | — |
| | 1-A | 19,625 | 7 | — | — |
| | 1-A | 19,625 | 11 | — | — |
| | 1-A | 19,625 | 9 | — | — |
| | 1-B | 19,625 | 42 | — | — |
| | 1-B | 19,625 | 12 | — | — |
| | 1-B | 19,625 | 10 | — | — |
| | 2-A | 19,625 | 19 | 4 | — |
| | 2-A | 19,625 | 18 | 4 | — |
| | 2-A | 19,625 | 17 | 19 | — |
| | 2-A | 19,625 | 7 | 3 | — |
| | 2-B | 19,625 | 16 | 2 | — |
| | 2-B | 19,625 | 21 | 1 | — |
| | 2-B | 19,625 | 25 | 1 | — |
| | 3-A | 19,625 | 9 | 2 | 1 |
| | 3-A | 19,625 | 13 | 2 | 1 |
| | 3-A | 19,625 | 10 | 2 | 1 |
| | 3-A | 19,625 | 17 | 1 | 3 |
| | 3-B | 19,625 | 20 | 2 | 3 |
| | 3-B | 19,625 | 12 | 1 | 1 |
| | 3-B | 19,625 | 12 | 1 | 3 |
| ASI—I 4% (w/w) | 4-A | 19,625 | 16 | — | — |
| | 4-A | 19,625 | 5 | — | — |
| | 4-A | 19,625 | 10 | — | — |
| | 4-A | 19,625 | 7 | — | — |
| | 4-B | 19,625 | 13 | — | — |
| | 4-B | 19,625 | 9 | — | — |
| | 4-B | 19,625 | 12 | — | — |
| | 5-A | 19,625 | 10 | 1 | — |
| | 5-A | 19,625 | 8 | 0 (Healed) | — |
| | 5-A | 19,625 | 4 | 0 (Healed) | — |
| | 5-A | 19,625 | 6 | 1 | — |
| | 5-B | 19,625 | 5 | 1 | — |
| | 5-B | 19,625 | 9 | 0 (Healed) | — |
| | 5-B | 19,625 | 10 | 0 (Healed) | — |
| | 6-A | 19,625 | 14 | 1 | 1 |
| | 6-A | 19,625 | 14 | 0 (Healed) | 0 (Healed) |
| | 6-A | 19,625 | 15 | 0 (Healed) | 0 (Healed) |
| | 6-A | 19,625 | 7 | 4 (apse) | 2 (apse) |
| | 6-B | 19,625 | 4 | 0 (Healed) | 0 (Healed) |
| | 6-B | 19,625 | 4 | 0 (Healed) | 0 (Healed) |
| | 6-B | 19,625 | 5 | 0 (Healed) | 0 (Healed) |
| ASI—II 10% (w/w) | 7-A | 19,625 | 6 | — | — |
| | 7-A | 19,625 | 7 | — | — |
| | 7-A | 19,625 | 8 | — | — |
| | 7-A | 19,625 | 10 | — | — |
| | 7-B | 19,625 | 8 | — | — |
| | 7-B | 19,625 | 7 | — | — |
| | 7-B | 19,625 | 8 | — | — |
| | 8-A | 19,625 | 16 | 0 (Healed) | — |
| | 8-A | 19,625 | 6 | 1 | — |
| | 8-A | 19,625 | 3 | 0 (Healed) | — |
| | 8-A | 19,625 | 10 | 0 (Healed) | — |
| | 8-B | 19,625 | 21 | 0 (Healed) | — |
| | 8-B | 19,625 | 14 | 1 | — |
| | 8-B | 19,625 | 6 | 0 (Healed) | — |
| | 9-A | 19,625 | 15 | 0 (Healed) | 0 (Healed) |
| | 9-A | 19,625 | 18 | 3 | 0 (Healed) |
| | 9-A | 19,625 | 5 | 0 (Healed) | 0 (Healed) |
| | 9-A | 19,625 | 7 | 0 (Healed) | 1 |
| | 9-B | 19,625 | 9 | 0 (Healed) | 0 (Healed) |
| | 9-B | 19,625 | 8 | 1 | 0 (Healed) |
| | 9-B | 19,625 | 8 | 1 | 1 |

TABLE 5

Effect of 5-day topical application of ASI on the biochemical parameters

| | 5th day | | |
|---|---|---|---|
| ASI | 0 | 4% (w/w) | 10% (w/w) |
| BUN, mg/dL | 30.87 ± 1.24 | 32.20 ± 1.11 | 30.07 ± 2.69 |
| CHOL, mg/dL | 78.86 ± 5.11 | 92.71 ± 7.75 | 81.86 ± 7.66 |
| HDL, mg/dL | 11.29 ± 0.64 | 9.86 ± 0.59 | 14.57 ± 2.86 |
| TRIG, mg/dL | 115.71 ± 7.73 | 152.71 ± 18.88 | 112.00 ± 7.80 |
| AST, μ/L | 288.14 ± 30.74 | 319.00 ± 25.02 | 309.86 ± 32.69 |
| GLU, mg/dL | 110.14 ± 3.48 | 98.29 ± 4.31 | 105.57 ± 6.59 |
| ALT, μ/L | 62.00 ± 4.73 | 66.86 ± 5.86 | 64.86 ± 7.85 |
| ALP, μ/L | 872.86 ± 141.13 | 993.86 ± 264.85 | 706.43 ± 113.24 |
| ALB, g/dL | 3.11 ± 0.12 | 3.36 ± 0.19 | 3.59 ± 0.20 |
| TBIL, mg/dL | 0.31 ± 0.02 | 0.47 ± 0.11 | 0.35 ± 0.03 |
| TP, g/dL | 6.10 ± 0.22 | 6.20 ± 0.21 | 6.49 ± 0.36 |
| AMY, μ/L | 725.57 ± 40.08 | 780.86 ± 36.11 | 831.43 ± 63.43 |
| LDL, mg/dl | 44.43 ± 3.85 | 52.14 ± 5.04 | 45.14 ± 5.54 |

TABLE 6

Effect of 10-day topical application of ASI on the biochemical parameters

| | 10th day | | |
|---|---|---|---|
| ASI | 0 | 4% (w/w) | 10% (w/w) |
| BUN, mg/dL | 28.57 ± 1.46 | 30.36 ± 1.47 | 29.83 ± 1.07 |
| CHOL, mg/dL | 93.86 ± 5.56 | 93.57 ± 10.61 | 94.29 ± 7.44 |
| HDL, mg/dL | 11.43 ± 0.78 | 14.71 ± 1.39 | 13.00 ± 1.29 |
| TRIG, mg/dL | 123.14 ± 7.90 | 117.43 ± 15.86 | 128.14 ± 7.40 |
| AST, μ/L | 252.00 ± 37.38 | 322.43 ± 33.44 | 296.71 ± 52.43 |
| GLU, mg/dL | 94.00 ± 2.07 | 93.43 ± 3.37 | 97.14 ± 5.19 |
| ALT, μ/L | 72.14 ± 1.97 | 77.86 ± 5.81 | 78.29 ± 4.12 |
| ALP, μ/L | 626.57 ± 150.81 | 801.71 ± 94.77 | 772.57 ± 90.29 |
| ALB, g/dL | 3.54 ± 0.11 | 3.53 ± 0.09 | 3.59 ± 0.18 |
| TBIL, mg/dL | 0.24 ± 0.02 | 0.24 ± 0.02 | 0.24 ± 0.02 |
| TP, g/dL | 6.44 ± 0.13 | 6.19 ± 0.14 | 6.97 ± 0.41 |
| AMY, μ/L | 616.43 ± 83.32 | 637.89 ± 113.25 | 821.00 ± 48.22 |
| LDL, mg/dl | 58.00 ± 4.49 | 55.57 ± 8.12 | 49.71 ± 6.22 |

TABLE 7

Effect of 15-day topical application of ASI on the biochemical parameters

| | 15th day | | |
|---|---|---|---|
| ASI | 0 | 4% (w/w) | 10% (w/w) |
| BUN, mg/dL | 28.90 ± 1.81 | 28.49 ± 3.65 | 28.59 ± 2.58 |
| CHOL, mg/dL | 94.00 ± 6.39 | 88.43 ± 11.84 | 72.00 ± 5.16 |
| HDL, mg/dL | 11.14 ± 0.51 | 16.14 ± 3.62 | 10.29 ± 0.57 |
| TRIG, mg/dL | 175.14 ± 10.12 | 159.29 ± 36.37 | 135.71 ± 8.76 |
| AST, μ/L | 191.00 ± 24.26 | 177.86 ± 38.01 | 163.57 ± 41.71 |
| GLU, mg/dL | 119.57 ± 3.58 | 125.14 ± 19.97 | 110.14 ± 4.34 |
| ALT, μ/L | 89.00 ± 4.49 | 92.29 ± 15.12 | 76.86 ± 5.76 |
| ALP, μ/L | 956.57 ± 126.03 | 985.71 ± 184.98 | 663.86 ± 89.42 |
| ALB, g/dL | 3.91 ± 0.08 | 3.73 ± 0.41 | 3.53 ± 0.15 |
| TBIL, mg/dL | 0.2 ± 0.01 | 0.19 ± 0.02 | 0.17 ± 0.01 |
| TP, g/dL | 7.13 ± 0.19 | 11.96 ± 5.60 | 6.34 ± 0.12 |
| AMY, μ/L | 1120.14 ± 37.40 | 1038.71 ± 115.48 | 1028.29 ± 70.23 |
| LDL, mg/dl | 47.86 ± 5.03 | 39.71 ± 4.97 | 34.71 ± 4.98 |

Figure 2:
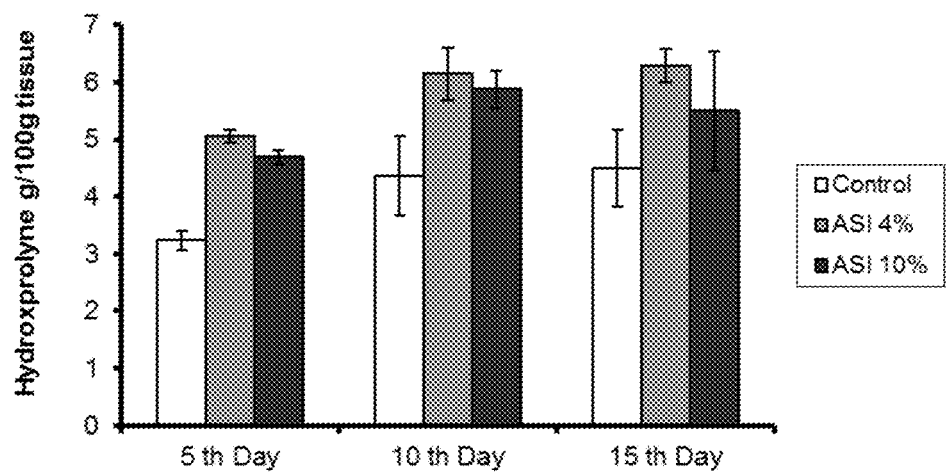
FIG. 2: Is a bar graph showing the effect of topical application of different doses of ASI on hydroxyproline concentration at 5th, 10th and 15th days after wound formation.

Results:

As can be seen in FIG. 1, the wounds in the ASI treated animals healed quicker than the control. Surprisingly, the 4% (w/w) ASI cream worked better than the 10% (w/w) ASI cream. Hydroxyproline is a major component of protein collagen. FIG. 2 shows that hydroxyproline concentration in the treatment area increased in the ASI treated animals compared to control. Surprisingly, the 4% (w/w) ASI cream increased hydroxyproline concentration to a greater extent that the 10% (w/w) ASI cream. Accordingly, topical application of ASI may increase hydroxyproline levels in the treatment area.

No mortality was observed during this study and all rats survived until the end of the study. The wounds in the control group displayed a greater degree of inflammation compared with ASI groups. The wound sites in ASI treated rats produced less exudate than the control wounds.

Figure 17:
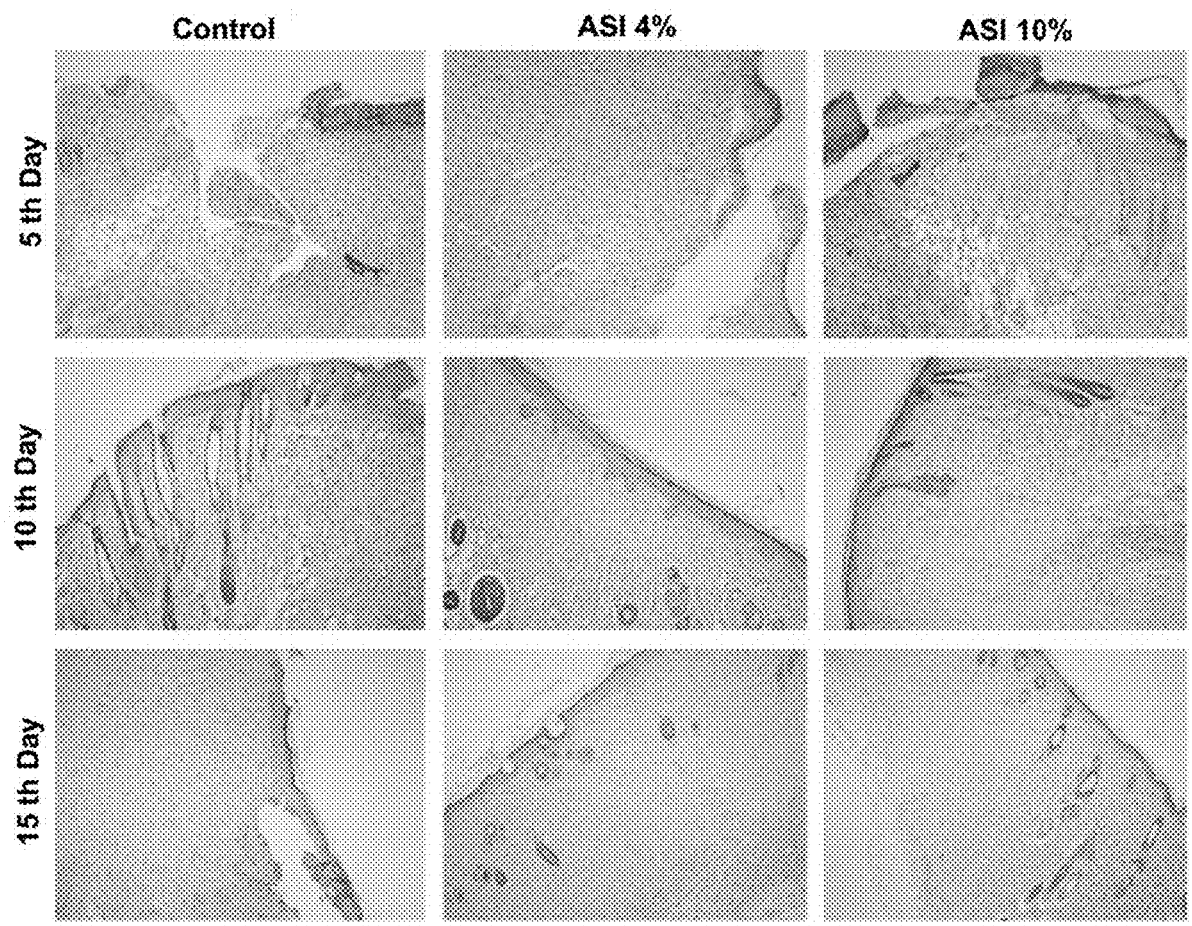
FIG. 17: shows histology sections demonstrating the effect of topical application of ASI on wound healing. Representative sections from the control group (no treatment), ASI 4% group (topical application of 4.4% ASI (w/w)), and ASI %10 group (topical application of 10% ASI (w/w)) one day 0, 5, 10, and 15 are shown.

Filling of the wound with granulation tissue to skin level was significantly slower in the control group than in the ASI groups (FIG. 1 and Tables 1-3). The mean unhealed wound area was significantly smaller and the mean percentage of total wound healing was significantly higher in the ASI-treated wounds than in the control wound (P<0.05). The wound area on completion of 15 days of treatment was 0.85 in the ASI 4% (w/w) treated group, when compared with 9.46, as observed in untreated rats (Table 2). The percent of wound contraction was also maximum in ASI 4% (w/w) treated rats (Table 3). The histopathology of the skin tissue corroborated with the macroscopic findings. In all rats, the healed wound surfaces were covered with a thick epithelial layer. Commonly mononuclear leukocyte type cellular infiltration was seen (FIG. 17).

Figure 4:
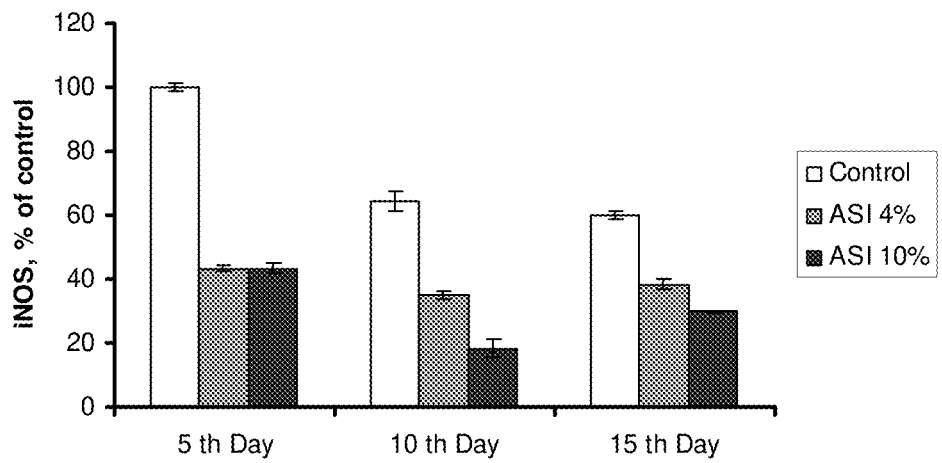
FIG. 4—inducible nitric oxide synthase ("iNOS")
Figure 5:
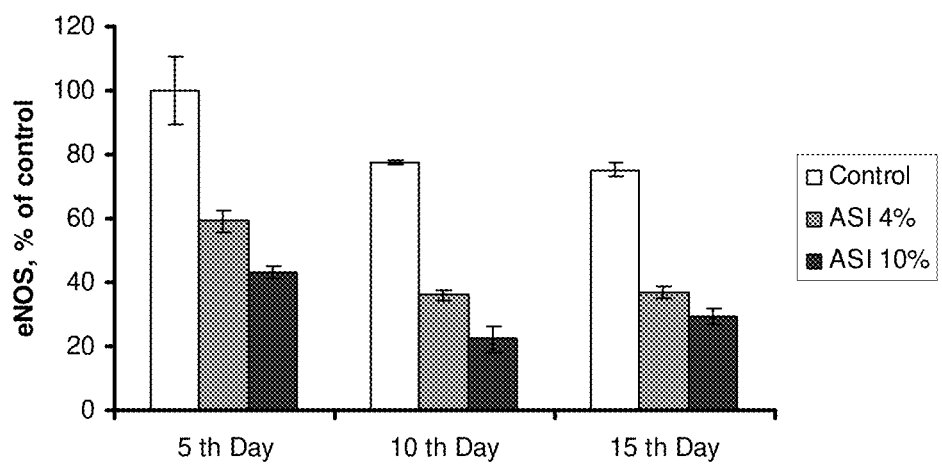
FIG. 5—endothelial nitric oxide synthase ("eNOS")

FIG. 4 shows that inducible nitric oxide synthase levels in the treatment area decreased in the ASI treated animals compared to control. Accordingly, topical application of ASI may decrease inducible nitric oxide synthase levels. FIG. 5 shows that endothelial nitric oxide synthase levels in the treatment area decreased in the ASI treated animals compared to control. Accordingly, topical application of ASI may decrease endothelial nitric oxide synthase levels.

Figure 6:
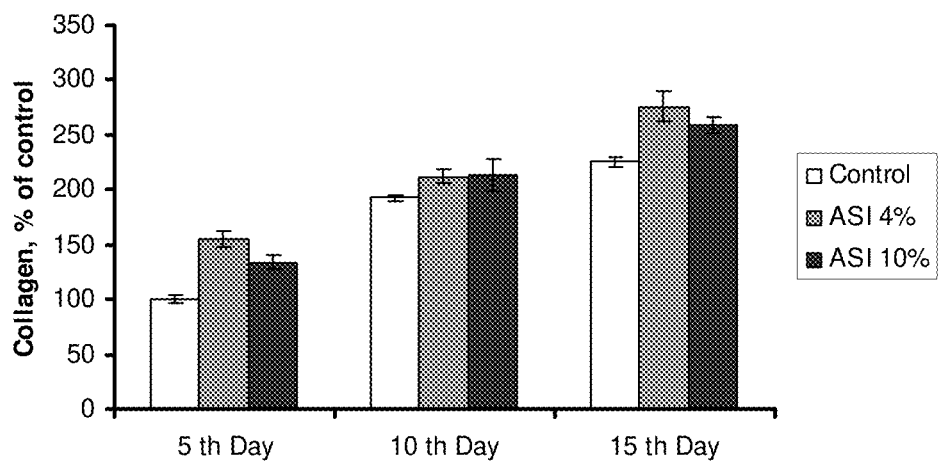
FIG. 6—collagen.

FIG. 6 shows that collagen levels in the treatment area increased in the ASI treated animals compared to control. Surprisingly, the 4% ASI (w/w) cream increased collagen levels to a greater extent that the 10% ASI (w/w) cream. Accordingly, topical application of ASI may hydroxyproline levels. Accordingly, topical application of ASI may increase collagen levels in the treatment area.

Figure 7:
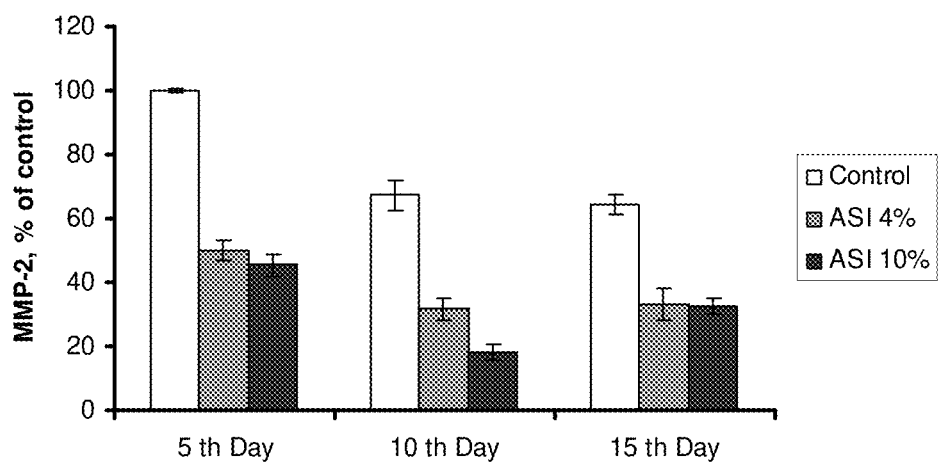
FIG. 7—matrix metalloproteinase-2 ("MMP-2")
Figure 8:
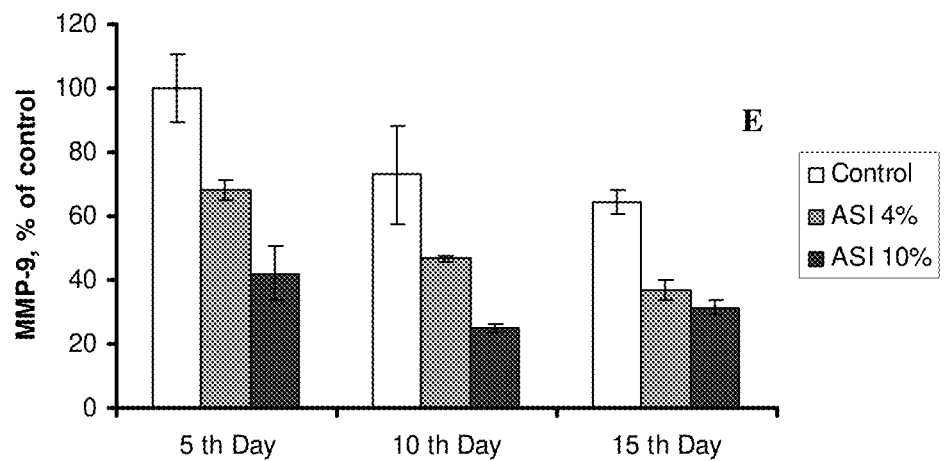
FIG. 8—matrix metalloproteinase-9 ("MMP-9")

FIG. 7 shows that MMP-2 levels in the treatment area decreased in the ASI treated animals compared to control. Accordingly, topical application of ASI may decrease MMP-2 levels in the treatment area. FIG. 8 shows that MMP-9 levels in the treatment area decreased in the ASI treated animals compared to control. Accordingly, topical application of ASI may decrease MMP-9 levels in the treatment area.

Figure 9:
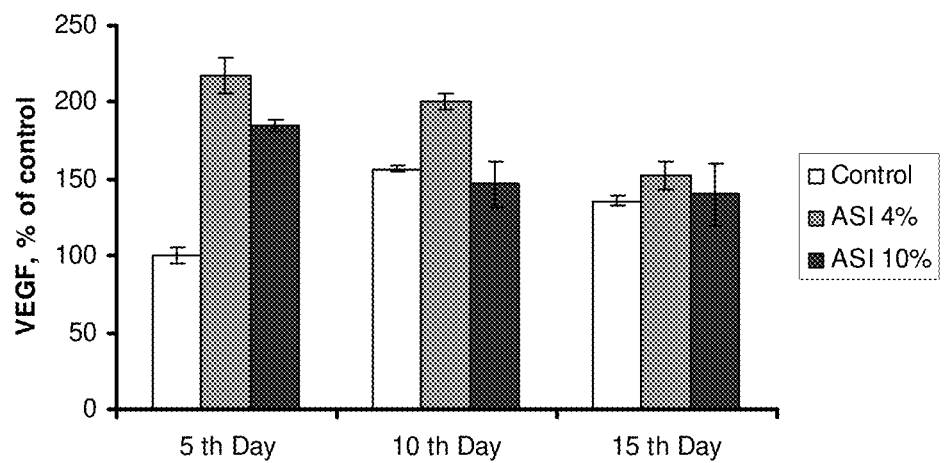
FIG. 9—vascular endothelial growth factor ("VEGF")
Figure 10:
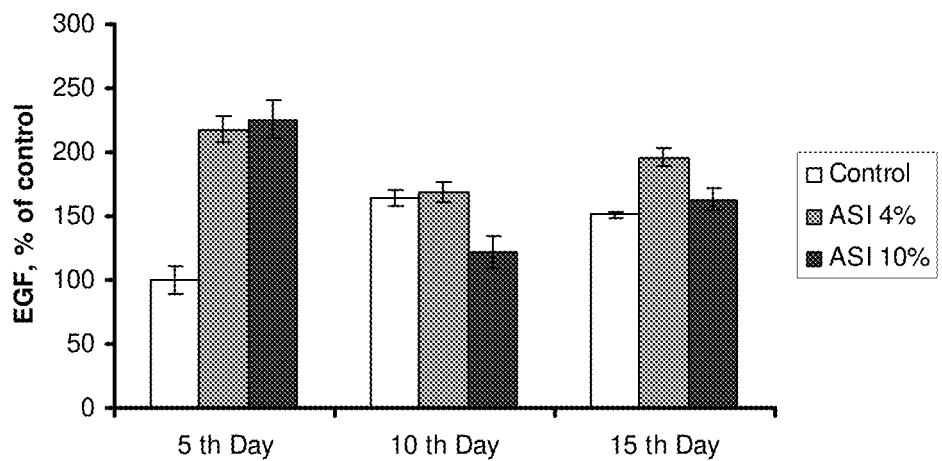
FIG. 10—endothelial growth factor ("EGF")
Figure 11:
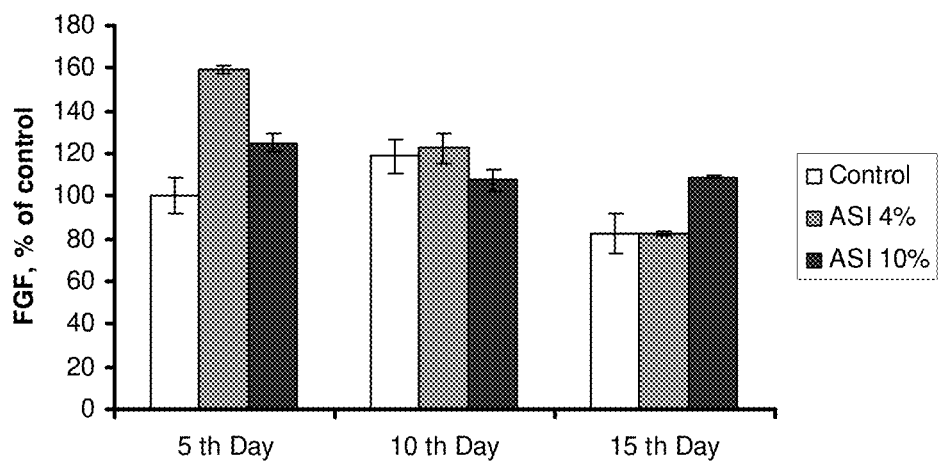
FIG. 11—and fibroblast growth factor ("FGF").
Figure 13:
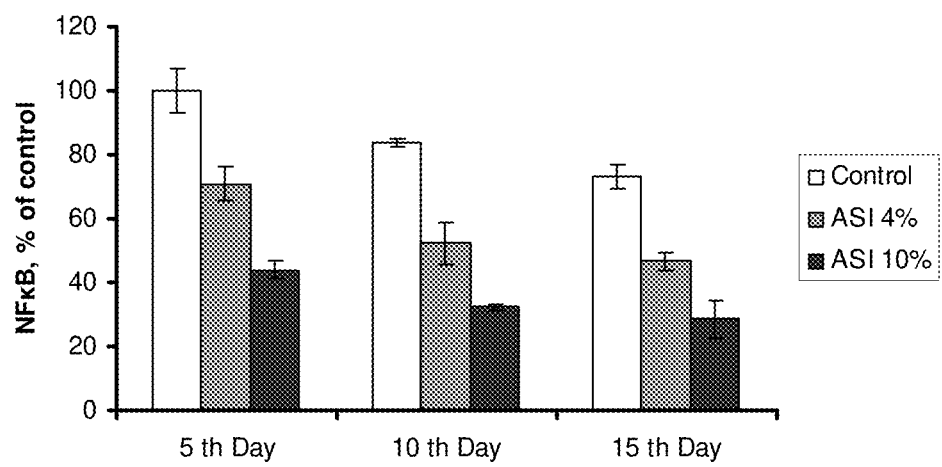
FIG. 13—NFκB.
Figure 14:
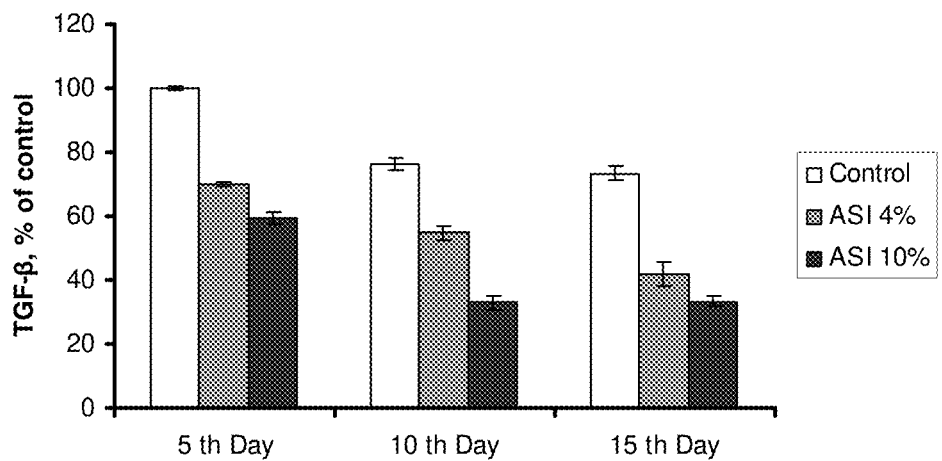
FIG. 14—TGF-β.
Figure 15:
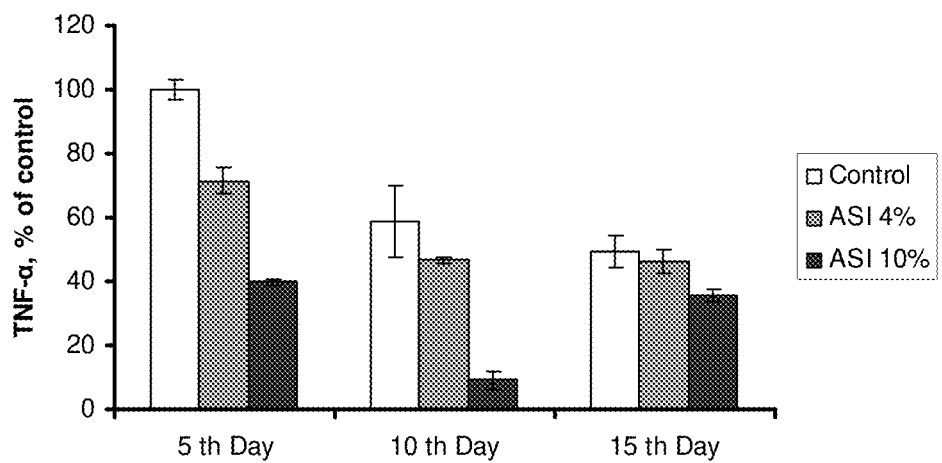
FIG. 15—TNF-α.
Figure 16:
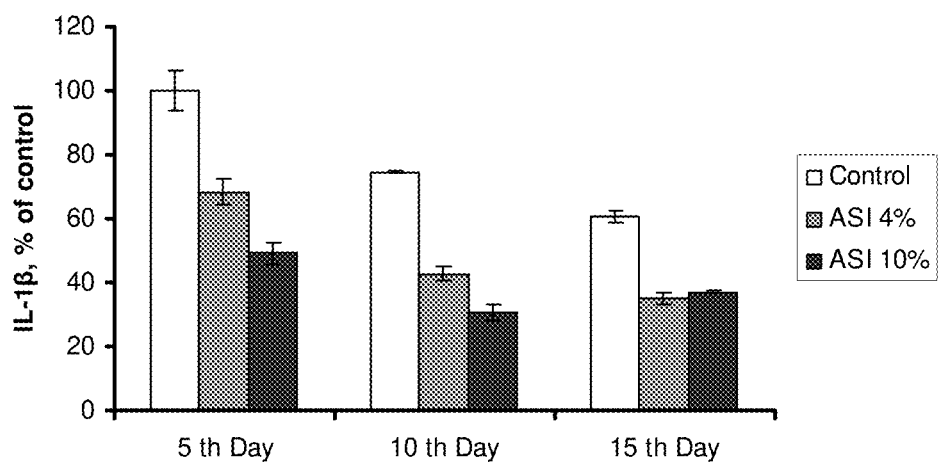
FIG. 16—IL-1β.

FIG. 9 shows that VEGF levels in the treatment area increased in the ASI treated animals compared to control. Surprisingly, the 4% ASI (w/w) cream increased VEGF levels to a greater extent that the 10% ASI (w/w) cream. Accordingly, topical application of ASI may increase VEGF levels in the treatment area. FIG. 10 shows that EGF levels in the treatment area increased in the ASI treated animals compared to control. FIG. 13 shows that NFκB levels decreased in the treatment area when compared to control. Accordingly, topical application of ASI may decrease NFκB levels in the treatment area. FIG. 14-15 shows that TGF-β and TNF-α levels decreased in the treatment area when compared to control. Accordingly, topical application of ASI may decrease TGF-β and TNF-α levels in the treatment area. FIG. 16 shows that IL-1β levels decreased in the treatment area when compared to control. Accordingly, topical application of ASI may decrease IL-1β levels in the treatment area.

It was also noted during qualitative examination that the hair on the shaved portion of the rat grew back at a faster rate in the ASI treatment groups than in the control group.

As can be seen in FIG. 2, the topical application of ASI caused a significant increase in hydroxyproline content, with the maximum increase reported with 4% ASI (w/w) on day 10, which remained at the increased level on day 15; although in 10% ASI (w/w) group, there was a small drop in hydroxyproline content ($P<0.01$). The results of hydroxyproline content corroborated with collagen measured in the wound area (FIG. 6).

Matrix metalloproteinases (MMP), both MMP-2 and MMP-9, registered a drop in ASI treated animals. MMP-2 and MMP-9 decreased most significantly on day 10 in rats treated with 10% ASI (w/w). Although on day 15, the level of MMP-2 was almost same at both (4% or 10%, (w/w)) dose levels of ASI (FIGS. 7-8; $P<0.05$). The results, which indicated tissue remodelling, were consistent with the histological findings (FIG. 17).

There was a significant decrease in iNOS at 10% ASI (w/w) on day 10. ASI 4% (w/w) also caused a reduction in iNOS expression, but to a less extent than ASI 10% (w/w) (FIG. 4; $P<0.001$). On day 15, however, iNOS increased to some extent, but was still significantly lower than the iNOS level in ASI 4% (w/w) treated animals ($P<0.05$). Overall, ASI caused a decrease in iNOS. The eNOS also showed a similar activity pattern (FIG. 5). The expression of VEGF increased in all groups when compared with the control (FIG. 9; $P<0.05$). The increase was maximum on day 5 in 4% ASI (w/w) treated rats. With time, the study reported a decrease in ASI on day 10 and 15.

Figure 3:
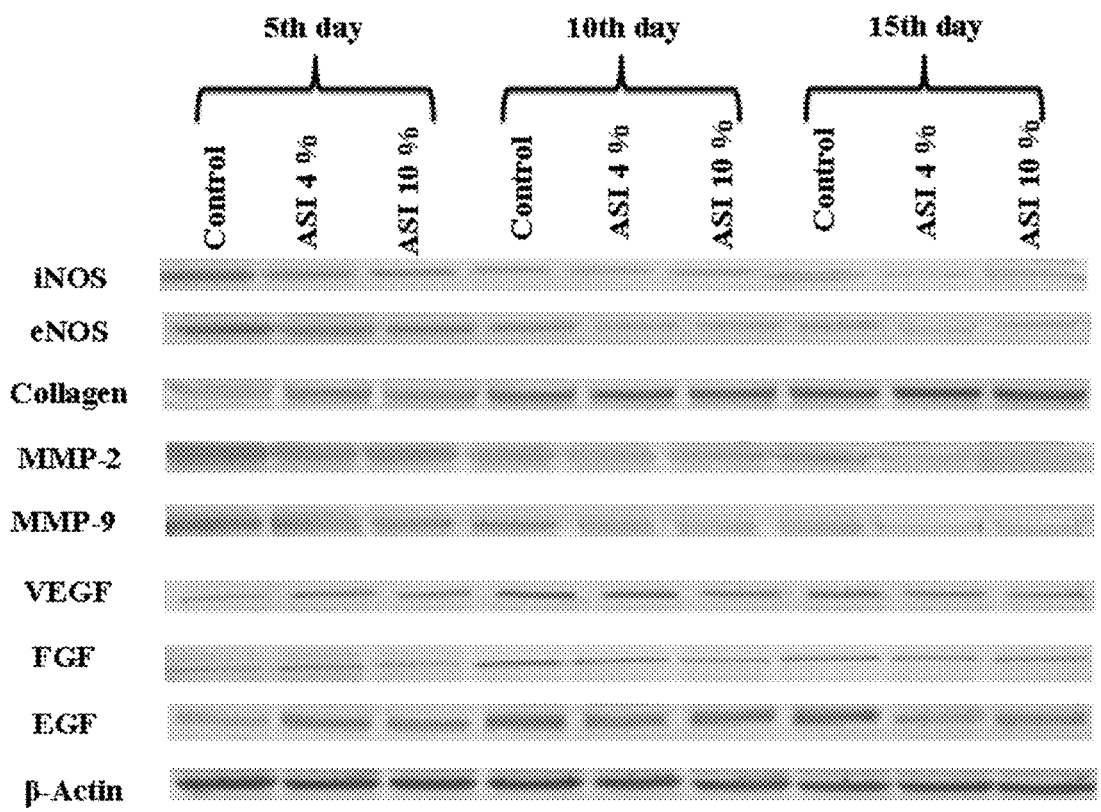
FIG. 3: Is a set of photographs of gels showing the effect of topical application of different doses of ASI on proteins involved in inflammation and wound healing at 5th, 10th and 15th days after wound formation. Each band is graphically depicted in FIGS. 4-12 below.

EGF and FGF were also measured in this study. There was an increase in EGF in all groups, with maximum increase being achieved in ASI treated animals on day 5. Subsequently, the level decreased on day 10 (FIG. 10). FGF also showed a similar pattern of activity. It increased on day 5 maximally in ASI 4% (w/w) group, but decreased with time, that is, on day 10 and 15 (FIG. 11; $P<0.05$). The Western blot analysis of all the above mentioned proteins is shown in FIG. 3.

Figure 12:
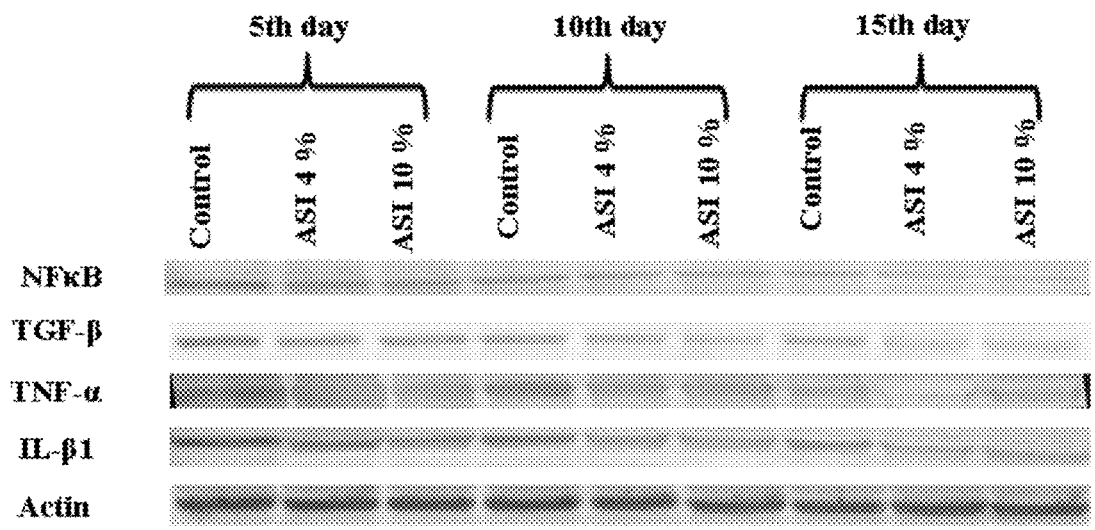
FIG. 12: Is a set of photographs of gels showing the effect of topical application of different doses of ASI on expression levels of proteins involved in inflammation and wound healing at 5th, 10th and 15th days after wound formation. Each band is graphically depicted in FIGS. 13-16 below.

As shown in FIG. 13, there was an increase in NF-κB expression in control group on day 5, which reduced at its own on day 10 and 15 ($P<0.001$). ASI treated animals, on the other hand, registered a significant decrease in NF-κB on day 5, which further decreased on day 10 and 15, with maximum decrease observed on day 15 at 10% ASI (w/w) ($P<0.05$). The TGF-β also showed a similar pattern of activity, with ASI causing a decrease in activity when compared with the control on respective days (FIG. 13, $P<0.05$). The TNF-α was at its lowest in ASI 10% (w/w) treated animals on day 10 (FIG. 14, $P<0.05$). The activity of TNF-α in ASI 10% (w/w) group, however, increased on day 15, but was significantly lower when compared with the control value on day 15. ASI treatment also caused a decrease in the level of IL-1β (FIG. 16, $P<0.05$). The Western blot panel showing the expression level of various proteins is shown in FIG. 12.

Generic Procedure for Examples 2-7

Animals:

In this study, 42 male, 4 months old, Wistar albino rats weighing between 250 and 300 g will be used. Animals will be housed at 21° C. with a day/night cycle of 12 h. During the study these animals will be fed ad libitum standard rodent feed. Guidelines for the care and use of animals approved by the relevant institution were followed and the local ethics committee approved this study.

Anesthesia:

The rats will be anaesthetized with single intramuscular injection of 6 mg/kg xylazine hydrochloride (Rompun, Bayer, 23.32 mg/ml) and 85 mg/kg ketamine hydrochlorure (Ketalar, Parke-Davis, 50 mg/ml).

Test Drugs:

4% and 10% arginine-silicate inositol (ASI) (w/w) ointment and cold cream (Botafarma, 12.5% spermaceti+12% white wax+56% liquid paraffin+0.5% borate of soda+19% distilled water) will be used in this study.

The rats will be divided into 2 main groups that each group will have randomly selected 21 rats. Each main group will be divided within themselves into 3 subgroups of 7 rats each to perform postoperative 5, 10 and 14 days of examination. Immediately after the wounds will be made (as described in Examples 2-7), the wounded areas in the first (n=21) and second (n=21) will be covered with cold cream (Botafarma, 12.5% spermaceti+12% white wax+56% liquid paraffin+0.5% borate of soda+19% distilled water) (Control) and 4% or 10% arginine-silicate inositol (ASI) (w/w) ointment twice a day, respectively. These applications will be repeated every day. The wounds will be clinically observed in all groups every day. The rats that completes postoperative follow-up periods of 5 (7 rats from each group), 10 (7 rats from each group) and 14 days (7 rats from each group) will be sacrificed.

For Examples 2-6, injured skin tissue samples undergo histopathological examination. The samples will be collected after sacrificing the rats for histopathological examination purposes. These tissue samples will be fixed in 10% neutral buffered formalin solution, embedded in paraffin wax, cut into 5 µm-thick sections and stained with haematoxyline-eosin and Masson's trichrome stain for examination by light microscopy.

Histological scoring will be assigned in a blinded manner as described previously (Greenhalgh et al., 1990; Asai et al., 2013). Briefly, each specimen will be given a score of 1-12: 1-3, none to minimal cell accumulation and granulation tissue or epithelial migration; 4 to 6, thin, immature granulation dominated by inflammatory cells, but with few fibroblasts, capillaries or collagen deposition and minimal epithelial migration; 7-9, moderately thick granulation tissue, ranging from domination by inflammatory cells to more fibroblasts and collagen deposition; and 10-12, thick vascular granulation tissue dominated by fibroblasts and extensive collagen deposition.

Statistical Analyses:

The thickness of granulation tissue will be examined and recorded at the center of each wound. Statistically, all data are expressed in millimeters as mean±standard error. The differences between days 5, 10 and 14 will be compared using the Mann Whitney U test. The differences between groups will be compared using the Kruskal-Wallis test. Statements of statistical significance are based on P<0.05. These analyses will be carried out using SPSS statistical analysis system (Release 10.0, SPSS. Inc).

Example 2

Wound Model:

The dorsal surfaces of the rats will be shaved and prepared with 10% antiseptic povidone-iodine solution (Kim-Pa, Pov-iiodeks, % 10 povidone-iodine). Then a surgical cautery will be used to create a full-thickness burn wound.

Measurements:

On every bandage change, the wound boundaries will be traced on a transparent sheet with a fine-tipped permanent marker. These transparent sheets will be scanned and the areas of wound sites and epithelization fronts will be measured with the help of the paint-brush (PB) computer program. The data obtained will be calculated with the following formula: Area $(cm^2)$=P/K·M, where P is the value of a particular wound site obtained on the PB, K is a rate constant for expressing the values of the PB as $cm^2$, and M is the magnitude of tracings after scanning. During the qualitative examination, the expansion rate, the day wound contraction started, the fraction of the wound healed with contraction, the rate of wound contraction, the day epithelization will be first noticed, the fraction of wound healed with epithelization (final wound size) and the number of days in which wound healing will be fully completed will be evaluated. The statistical comparison will be made with ANOVA. The results will be considered significant at P<0.05 and a 95% confidence interval (Kiliç et al., 2002).

Example 3

Wound Model:

The dorsal surfaces of the rats will be shaved and prepared with 10% antiseptic povidone-iodine solution (Kim-Pa, Pov-iiodeks, % 10 povidone-iodine). Then the rats will be given a 5 cm by 5 cm abrasion wound.

Measurements:

On every bandage change, the wound boundaries will be traced on a transparent sheet with a fine-tipped permanent marker. These transparent sheets will be scanned and the areas of wound sites and epithelization fronts will be measured with the help of the paint-brush (PB) computer program. The data obtained will be calculated with the following formula: Area $(cm^2)$=P/K·M, where P is the value of a particular wound site obtained on the PB, K is a rate constant for expressing the values of the PB as $cm^2$, and M is the magnitude of tracings after scanning. During the qualitative examination, the expansion rate, the day wound contraction started, the fraction of the wound healed with contraction, the rate of wound contraction, the day epithelization will be first noticed, the fraction of wound healed with epithelization (final wound size) and the number of days in which wound healing will be fully completed will be evaluated. The statistical comparison will be made with ANOVA. The results will be considered significant at P<0.05 and a 95% confidence interval (Kiliç et al., 2002).

Example 4

Wound Model:

The dorsal surfaces of the rats will be shaved and prepared with 10% antiseptic povidone-iodine solution (Kim-Pa, Pov-iiodeks, % 10 povidone-iodine). Then a surgical trochar will be used to create three distinct 2 cm deep puncture wounds.

Measurements:

On every bandage change, the wound boundaries will be traced on a transparent sheet with a fine-tipped permanent marker. These transparent sheets will be scanned and the areas of wound sites and epithelization fronts will be measured with the help of the paint-brush (PB) computer program. The data obtained will be calculated with the following formula: Area $(cm^2)$=P/K·M, where P is the value of a particular wound site obtained on the PB, K is a rate constant for expressing the values of the PB as $cm^2$, and M is the magnitude of tracings after scanning. During the qualitative examination, the expansion rate, the day wound contraction started, the fraction of the wound healed with contraction, the rate of wound contraction, the day epithelization will be first noticed, the fraction of wound healed with epithelization (final wound size) and the number of days in which wound healing will be fully completed will be evaluated. The statistical comparison will be made with ANOVA. The results will be considered significant at P<0.05 and a 95% confidence interval (Kiliç et al., 2002).

Example 5

Wound Model:

The dorsal surfaces of the rats will be shaved and prepared with 10% antiseptic povidone-iodine solution (Kim-Pa, Pov-iiodeks, % 10 povidone-iodine). Then the rats will be given a 5 cm by 5 cm abrasion wound. The ASI treatment in this example is provided as the 4% or 10% ASI (w/w) formulations described above, but embedded into the bandage itself.

Measurements:

On every bandage change, the wound boundaries will be traced on a transparent sheet with a fine-tipped permanent marker. These transparent sheets will be scanned and the areas of wound sites and epithelization fronts will be measured with the help of the paint-brush (PB) computer program. The data obtained will be calculated with the following formula: Area $(cm^2)$=P/K·M, where P is the value of a particular wound site obtained on the PB, K is a rate constant for expressing the values of the PB as $cm^2$, and M is the magnitude of tracings after scanning. During the qualitative examination, the expansion rate, the day wound contraction started, the fraction of the wound healed with contraction, the rate of wound contraction, the day epithelization will be first noticed, the fraction of wound healed with epithelization (final wound size) and the number of days in which wound healing will be fully completed will be evaluated. The statistical comparison will be made with ANOVA. The results will be considered significant at P<0.05 and a 95% confidence interval (Kiliç et al., 2002).

Example 6

Wound Model:

The dorsal surfaces of the rats will be shaved and prepared with 10% antiseptic povidone-iodine solution (Kim-Pa, Poviiodeks, % 10 povidone-iodine). Then a portacath (infusing normal saline) will be installed.

Measurements:

On every bandage change, the wound boundaries will be traced on a transparent sheet with a fine-tipped permanent marker. These transparent sheets will be scanned and the areas of wound sites and epithelization fronts will be measured with the help of the paint-brush (PB) computer program. The data obtained will be calculated with the following formula: Area $(cm^2)$=P/K·M, where P is the value of a particular wound site obtained on the PB, K is a rate constant for expressing the values of the PB as $cm^2$, and M is the magnitude of tracings after scanning. During the qualitative examination, the expansion rate, the day wound contraction started, the fraction of the wound healed with contraction, the rate of wound contraction, the day epithelization will be first noticed, the fraction of wound healed with epithelization (final wound size) and the number of days in which wound healing will be fully completed will be evaluated. The statistical comparison will be made with ANOVA. The results will be considered significant at P<0.05 and a 95% confidence interval (Kiliç et al., 2002).

Example 7

Wound Model:

The dorsal surfaces of the rats will be shaved.

Measurements:

Twice each day, the shaved boundaries will be traced on a transparent sheet with a fine-tipped permanent marker. These transparent sheets will be scanned and the areas of hair growth fronts will be measured with the help of the paint-brush (PB) computer program. The data obtained will be calculated with the following formula: Area $(cm^2)$=P/K·M, where P is the value of a particular site obtained on the PB, K is a rate constant for expressing the values of the PB as $cm^2$, and M is the magnitude of tracings after scanning. During the qualitative examination, the expansion rate of hair and general appearance of the regrown hair will be noted. Also, twice each day, the length of the regrown hair will be measured. The statistical comparison will be made with ANOVA. The results will be considered significant at P<0.05 and a 95% confidence interval (Kiliç et al., 2002).

Statistical Analyses:

The length of regrown hair will be examined and recorded at the center of each shaved area. Statistically, all data are expressed in millimeters as mean±standard error. The differences between days 2, 7 and 14 will be compared using the Mann Whitney U test. The differences between groups will be compared using the Kruskal-Wallis test. Statements of statistical significance are based on P<0.05. These analyses will be carried out using SPSS statistical analysis system (Release 10.0, SPSS. Inc).

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of ASI" for the treatment of wounds or for promoting hair growth would not include other active ingredients known to promote wound healing or known to improve hair growth, respectively.

Although the invention has been described with reference to embodiments and examples, it should be understood that numerous and various modifications can be made without departing from the spirit of the invention. Accordingly, the invention is limited only by the following claims.

What is claimed is:

1. A method for promoting hair growth comprising:
   orally administering a daily dose of a hair growth composition comprising inositol-stabilized arginine silicate to a human in need thereof;
   wherein the daily dose comprises about 1.0 mg to about 5.0 mg of the inositol-stabilized arginine silicate per kilogram of the human's body weight.

2. The method of claim 1, wherein the inositol-stabilized arginine silicate is between about 1% and about 10% by total weight of the hair growth composition.

3. The method of claim 2, wherein the inositol-stabilized arginine silicate is about 4% by total weight of the hair growth composition.

4. The method of claim 2, wherein the inositol-stabilized arginine silicate is 4.4% by total weight of the hair growth composition.

5. A method for increasing hair thickness comprising:
   orally administering a daily dose of a hair thickening composition comprising inositol-stabilized arginine silicate to a human in need thereof;
   wherein the daily dose comprises about 1.0 mg to about 5.0 mg of the inositol-stabilized arginine silicate per kilogram of the human's body weight.

6. The method of claim 5, wherein the inositol-stabilized arginine silicate is between about 1% by total weight and about 10% of the hair thickening composition.

7. The method of claim 6, wherein the inositol-stabilized arginine silicate is about 4% by total weight of the hair thickening composition.

8. The method of claim 6, wherein the inositol-stabilized arginine silicate is 4.4% by total weight of the hair thickening composition.

9. The method of claim 1, wherein the hair growth composition comprises a second active ingredient.

10. The method of claim 5, wherein the hair thickening composition comprises a second active ingredient.

11. The method of claim 1, wherein the subject is a female human.

12. The method of claim 5, wherein the subject is a female human.

13. The method of claim 1, wherein the method promotes hair growth in a shaved area.

14. The method of claim 1, wherein the method increases the rate of hair growth.

15. The method of claim 1, wherein the daily dose comprises about 1.0 mg, about 2.0 mg, about 3.0 mg, about 4.0 mg, or about 5.0 mg of the inositol-stabilized arginine silicate per kilogram of the subject's body weight.

16. The method of claim 5, wherein the daily dose comprises about 1.0 mg, about 2.0 mg, about 3.0 mg, about 4.0 mg, or about 5.0 mg of the inositol-stabilized arginine silicate per kilogram of the subject's body weight.

17. The method of claim 1, wherein the daily dose comprises about 1.0 mg to about 3.0 mg of the inositol-stabilized arginine silicate per kilogram of the subject's body weight.

18. The method of claim 5, wherein the daily dose comprises about 1.0 mg to about 3.0 mg of the inositol-stabilized arginine silicate per kilogram of the subject's body weight.

19. The method of claim 1, wherein the daily dose comprises about 2.0 mg of the inositol-stabilized arginine silicate per kilogram of the subject's body weight.

20. The method of claim 5, wherein the daily dose comprises about 2.0 mg of the inositol-stabilized arginine silicate per kilogram of the subject's body weight.

\* \* \* \* \*